(12) United States Patent
Liu et al.

(10) Patent No.: US 7,439,060 B1
(45) Date of Patent: Oct. 21, 2008

(54) INDEPENDENT HELPER VIRUS PACKAGING CELL LINE FOR PROPAGATING VIRAL VECTORS

(75) Inventors: Dakai Liu, Islip, NY (US); Elazar Rabbani, New York, NY (US)

(73) Assignee: Enzo Therapeutics, Inc., Farmingdale, NY (US)

( * ) Notice: Subject to any disclaimer, the term of this patent is extended or adjusted under 35 U.S.C. 154(b) by 0 days.

(21) Appl. No.: 09/046,833

(22) Filed: Mar. 24, 1998

Related U.S. Application Data

(62) Division of application No. 08/822,963, filed on Mar. 21, 1997, now abandoned.

(51) Int. Cl.
*C12N 5/10* (2006.01)
*A61K 48/00* (2006.01)
*C12N 15/63* (2006.01)

(52) U.S. Cl. .................... 435/325; 435/354; 435/366; 435/320.1; 536/23.1; 536/24.5

(58) Field of Classification Search .............. 435/320.1, 435/325, 352, 354, 363, 366, 369
See application file for complete search history.

(56) References Cited

U.S. PATENT DOCUMENTS

| 5,166,320 | A |   | 11/1992 | Wu et al. |  |
|---|---|---|---|---|---|
| 5,278,056 | A |   | 1/1994 | Bank et al. |  |
| 5,474,935 | A | * | 12/1995 | Chatterjee et al. | 435/320.1 |
| 5,650,309 | A |   | 7/1997 | Wong-Staal et al. |  |
| 5,658,776 | A | * | 8/1997 | Flotte et al. | 435/457 |
| 5,681,746 | A | * | 10/1997 | Bodner et al. | 435/350 |
| 5,686,279 | A | * | 11/1997 | Finer et al. | 435/172.3 |
| 5,814,500 | A | * | 9/1998 | Dietz | 435/172.3 |
| 5,856,152 | A |   | 1/1999 | Wilson et al. |  |
| 6,013,517 | A | * | 1/2000 | Respess et al. | 435/325 |
| 6,156,497 | A |   | 12/2000 | Kaleko et al. |  |
| 6,271,348 | B1 | * | 8/2001 | Bujard et al. | 530/350 |

FOREIGN PATENT DOCUMENTS

| EP |   | 128332 B1 | 8/1995 |
|---|---|---|---|
| EP |   | 07793652 A2 | 6/1997 |
| WO | WO 9506743 |   | 3/1995 |
| WO | WO 9613598 |   | 5/1996 |
| WO | WO 9636705 |   | 11/1996 |
| WO | WO9837917 |   | 9/1998 |

OTHER PUBLICATIONS

Salmons et al., Human Gene Therapy, vol. 4, pp. 129-141, 1993.*
Alan E. Smith, Annu. Rev. Microbiol., vol. 49, pp. 807-838, 1995.*
Strair et al., Nucleic Acids Res., 1993, vol. 21, No. 20, pp. 4836-4842.*
Morgenstern, J.P. et al, "Choice and Manipulation of Retroviral Vectors," *Gene Transfer and Expression Protocols. Methods in Molecular Biology*, vol. 7:181-193; (1991), Murray, E.J., Ed., The Humana Press, New Jersey.
Anderson, W.F, "Human Gene Therapy," *Science* 256:808-813 (1992).
Mulligan, R.C, "The Basic Science of Gene Therapy," *Science* 260:926-932(1993).
Smith, A.E, "Viral Vectors in Gene Therapy," *Ann Rev. Microbiol,* 49:807-38(1995).
Muzyczka, N, "Use of Adeno-Associated Virus as a General Transduction Vector for Mammalian Cells," *Current Topics in Microbiolgy and Immunolgy 158*:97-129.
Kotin, R.M, "Prospects for the Use of Adeno-Associated Virus as a Vector for Human Gene Therapy," *Human Gene Therapy 5*:793-801 (1994).
Emerman, M et al., "Genes with Promoters in Retrovirus Vectors Can Be Independently Suppressed by an Epigenetic Mechanism," *Cell 39*:459-467 (1984).
Emerman, M et al., "Quantitative Analysis of Gene Suprression in Integrated Retrovirus Vectors," *Molecular and Cellular Biology* 6(1):792-800 (1986).
Yu, S.F et al., "Self-inactivating retroviral vectors designed for transfer of whole genes into mammalian cells," *Proc. Natl. Acad. Sci. USA* 83:3194-3198 (1986).
Hawley, R.G. et al., "Handicapped retroviral vectors efficiently transduce foreign genes into hematopoietic stem cells," *Proc. Natl. Acad. Sci. USA 84*; 2406-2410 (1987).
Yee, J.K et al., "Gene expression from transcriptionally disabled retroviral vectors," *Proc. Natl. Acad. Sci. USA 84*:5197-5201 (1987).
Dougherty, J.P and Temin H.M., "A promoterless retroviral vector indicates that there are sequences in U3 required for 3' RNA processing," *Proc. Natl. Acad. Sci. USA 84*:1197-1201 (1987).
Whitcomb, J.M and Hughes, S.H., "Retroviral Reverse Transcription and integration: Progress and Problems" *Ann. Rev. Cell Biol. 8*:275-306 (1992).
Jaenisch, R et al., "Germline Integration of Moloney Murine Leukemia Virus at the Mov13 Locus Leads to Recessive Lethal Mutation and Early Embryonic Death," *Cell 32*:209-216 (1983).
Fung, Y.T. et al., "On the mechanism of retrovirus-induced avin lymphoid leucosis: Deletion and integration of the proviruses," *Proc. Natl. Acad, Sci. USA* 78(6):3418-3422 (1981).
Neel, B.G. and Hayward W.S., "Avian Leukosis Virus-Induced Tumors Have Common Proviral Integration Sites and Synthesize Discrete New RNAs: Oncogenesis by Promoter Insertion," *Cell 23*:323-334 (1981).

(Continued)

*Primary Examiner*—David Guzo
(74) *Attorney, Agent, or Firm*—Ronald C. Fedus, Esq.

(57) ABSTRACT

Provided are novel vectors and viral vectors capable of expressing exogenous gene or exogenous nucleic acid sequences in a target cell of interest, such as T cells, bone marrow cells, epithelial cells, liver cells and the like. The nucleic acid components of the vectors may include one or more native promoter/enhancer regions having modified sequence segments, one or more non-native promoter/enhancer or non-native promoter's gene or gene segment, and a native viral vector terminator or processing signal or segment thereof. The viral vectors comprise a virus or viral portion having on the surfaces or envelopes adsorption components, one for a packaging cell line and the other for delivery to a target cell. Packaging cell lines for propagating the vectors and viral vectors are also provided, as are novel processes for propagating any of the disclosed vectors or viral vectors.

27 Claims, 10 Drawing Sheets

OTHER PUBLICATIONS

Payne, G.S. et al., "Analysis of Avian Leukosis Virus DNA and RNA in Bursal Tumors: Viral Gene Expression is Not Required for Maintenance of the Tumor Stae," *Cell 23*:311-322 (1983).

Samulski, R.J et al., "Targeted integration of adeno-associated virus (AAV) into human chromosome 19," *The EMBO Journal 10*(12):3941-3950 (1991).

Kotin, R.M et al., "Mapping and Direct Visualization of a Region-Specific Viral DNA Integration Site on Chromosome 19q13-qter," *Genomics 10*:831-834 (1991).

Kotin et al., "Site-specific integration by adeno-associated virus," *Proc. Natl. Acad. Sci. USA 87*:2211-2215 (1990).

Manser, T. and Gesteland R.F., "Human U1 Loci: Genes for Human U1 RNA Have Dramatically Similar Genomic Envrionments." *Cell 29*:257-264 (1982).

Wells S. et al., "The presence of an autologous marrow stromal cell layer increases glucocerebrosidase gene transduction of long-term culture initiating cells (LTCICs) from the bone marrow of a patient with Gaucher disease," *Gene Therapy 2*:512-520 (1995).

Bertolini F. et al., "Engineered Stromal Layers and Continuous Flow Culture Enhance Multidrug Resistance Gene Transfer in Hematopoietic Progenitors," *Cancer Research 56*:2566-2572 (1996).

Xu L.C. et al., "Growth Factors and Stromal Support Generate Very Efficient Retroviral Transduction of Peripheral Blood CD34$^+$ Cells From Gaucher Patients." *Blood*, 86(1):141-146 (1995).

Nolta J.A. et al., "Analysis of Optimal Conditions for Retroviral-Medicated Transduction of Primitive Human Hematopoietic Cells," *Blood 86*(1):101-110 (1995).

Lever, A.M.L, "Gene therapy for HIV infection," *British Medical Bulletin*, 51(1):149-166 (1995).

Wu C.H. et al., "Targeting Genes: Delivery and Persistent Expression of a Foreign Gene Driven by Mammalian Regulatory Elements in Vivo" *J Biol Chem*, 264(29):16985-16987.

Wagner E. et al., "Coupling of adenovirus to transferring-polysine/DNA complexes greatly enhances receptor-mediated gene delivery and expression of transfected genes." *Proc. Natl. Acad. Sci. USA 89*: 6099-6103 (1992).

Ruoslahti E. et al., "Alignment of Biologically Active Domains in the Fibronectin Molecule," *The Journal of Biological Chemistry 256*(14):7277-7281 (1981).

Crisitiano R.J. et al., "Hepatic gene therapy: Adenovirus enhancement of receptor-mediated gene delivery and expression in primary hepatocytes," *Proc Natl. Acad. Sci. USA 90*:2122-2136.

Curiel D.T. et al., "Adenovirus enhancement of transferring-polysine-mediated gene delivery," *Proc. Natl. Acad. Sci. USA 88*:8850-8854 (1991).

Wagner E. et al., "Influenza virus hemagglutinin HA-2 N-terminal fusogenic peptides augment gene transfer by transferring-polysine-DNA complexes: Toward a synthetic virus-like gene-transfer vehicle," *Proc. Natl. Acad. Sci. USA 89*:7934-7938 (1992).

Zieve, G.W and Sauterer R.A., "Cell Biology of the snRNP Particles," *Biochemistry and Molecular Biology 25*(1):1-46 (1990).

Argos P. et al., "The integrase family of site-specific recombinases: regional similarities and global diversity," *The EMBO Journal 5*(2):433-440 (1986).

Sattentau, Q.J. and Weiss, R.A., "The CD4 Antigen: Physiological Ligand and HIV Receptor," *Cell 52*:631-633 (1988).

Craigle, R. et al., *Cell 62*:829-837 (1990).

Liu, D. et al., "Stable Human Immunodeficiency Virus Type 1 (HIV-1) Resistance in Transformed CD4$^+$ Monocytic Cells Treated with Multitargeting HIV-1 Antisense Sequences Incorporated into U1 snRNA," *Journal of Virology 71*(5):4079-4085 (1997).

Berkner, K.L., *Curr. Top. Microbiol. Immunol. 158*: 39-66 (1992).

Emerman, M. et al., *Nucleic Acid Res. 14*: 9361-9396 (1986).

Lewin, B. *Genes V*; Oxford University Press, New York (1994).

Sambrook, J., Fritsch, E.F. and Maniatis, T. *Molecular Cloning 2nd ed.* Cold Spring Laboratory, Cold Spring Harbor, NY, 1989.

Maddon, P.J et al., *Cell 47*:333-348 (1986).

Robinson, William S., "Hepadnaviridae and Their Replication," chapter in *Field's Virology*, vol. 2, edited by Fields, Bernard N., 2$^{nd}$ Edition, Ravens Press, pp. 2137-2169 (1990).

Miller, et al., *Biotechniques*, vol. 7(9):980-990 (1989).

Salmons, et al., "Targeting Retroviral Vectors for Gene Therapy," *Human Gene Therapy*, vol. 4:129-141 (1993).

Van Den Wollenberg, D., et al, *Gene*, vol. 144(2):238-241 (1994).

Choulika, A., et al, *Journal of Virology*, vol. 70(3):1792-1798 (1996).

Ferrari, G., et al, *Human Gene Therapy*, vol. 6(6):733-742 (1995).

Lund, A.H., et al, "Transcriptional silencing of retroviral vectors," *Journal of Biomedical Science*, vol. 3(6):365-378 (1996).

Robinson, D., et al, *Gene Therapy*, vol. 2(4):269-278 (1995).

Emi, H., et al., "Pseudotype formation of murine leukemia virus with the G protein of vesicular stomatitis virus," *Journal of Virology 65*:1202-1207 (1991).

Feng, M., et al., "Stable in vivo gene transduction via a novel adenoviral/retroviral chimeric vector," *Nature Biotechnology 15*:866-870 (1997).

Fisher, K.J., et al., "A novel adenovirus-adeno-associated virus hybrid vector that displays efficient rescue and delivery of the AAV genome," *Human Gene Therapy 7*:2079-2087 (1996).

Gerhardt, E., et al., "Phenotype mixing of rodent but not avian hepadnavirus surface proteins into human hepatitis B virus particles," *Journal of Virology 69*:1201-1208 (1995).

Johnston, K.M., et al., "HSV/AAV hybrid amplicon vectors extend transgene expression in human glioma cells," *Human Gene Therapy 8*:359-370 (1997).

Matano, T., et al., "Targeted infection of a retrovirus bearing a CD$-Env chimera into human cells expressing human immunodeficiency virus type 1," *Journal of General Virology 76*:3165-3169 (1995).

Vile, R.G., et al., "A murine cell line producing HTLV-1 pseudotype virions carrying a selectable marker gene," *Virology 180*:420-424 (1991).

* cited by examiner

Wild type 3' LTR sequence:

```
1    GAACAGATGG  AACAGCTGAA  TATGGGCCAA  ACAGGATATC  TGTGGTAAGC
51   AGTTCCTGCC  CCGGCTCAGG  GCCAAGAACA  GATGGAACAG  CTGAATATGG
101  GCCAAACAGG  ATATCTGTGG  TAAGCAGTTC  CTGCCCCGGC  TCAGGGCCAA
151  GAACAGATGG  TCCCCAGATG  CGGTCCAGCC  CTCAGCAGTT  TCTAGAGAAC
201  CATCAGATGT  TTCCAGGGTG  CCCCAAGGAC  CTGAAATGAC  CCTGTGCCTT
251  ATTTGAACTA  ACCAATCAGT  TCGCTTCTCG  CTTCTGTTCG  CGCGCTTCTG
301  CTCCCCGAGC  TCAATAAAA
```

Corresponding modified 3' LTR sequence from pENZ1
(modified sequences in bold italics):

```
1    ACGCTTGATC  CGGCTACCTG  CCCATTCGAC  CACCAAGCGA  AACATCGCAT
51   CGAGCGAGCA  CGTACTCGGA  TGGAAGCCGG  TCTTGTCGAT  CAGGATGATC
101  TGGACGAAGA  GCATCAGGGG  CTCGCGCCAG  CCGAACTGTT  CGCCAGGCTC
151  AAGGCGCGCA  TGCCCGACGG  CGAGGATCTC  GTCGTGACTT  TCTAGAGAAC
201  CATCAGATGT  TTCCAGGGTG  CCCCAAGGAC  CTGAAATGAC  CCTGTGCCTT
251  ATTTGAACTA  ACCGGTCAGT  TCGCTTCTCG  CTTCTGTTCG  CGCGCTTCTG
301  CTCCCCGAGC  TCAGCTGCG
```

FIG. 2

SEQUENCE LISTING

<160> NUMBER OF SEQ ID NOS: 16

<210> SEQ ID NO 1
<211> LENGTH: 9
<212> TYPE: DNA
<213> ORGANISM: Bacteriophage lambda
<220> FEATURE:
<223> OTHER INFORMATION: Description of Artificial Sequence:nucleic
      acid, double stranded, linear topology

<400> SEQUENCE: 1 tatcaccgc                                                               9

<210> SEQ ID NO 2
<211> LENGTH: 9
<212> TYPE: DNA
<213> ORGANISM: bacteriophage 434
<220> FEATURE:
<223> OTHER INFORMATION: Description of Artificial Sequence:nucleic
      acid, double stranded, linear topology

<400> SEQUENCE: 2 acaagaaaa                                                               9

<210> SEQ ID NO 3
<211> LENGTH: 10
<212> TYPE: DNA
<213> ORGANISM: Escherichia coli
<220> FEATURE:
<223> OTHER INFORMATION: Description of Artificial Sequence:nucleic
      acid, double stranded, linear topology

<400> SEQUENCE: 3
gtactagtta                                                             10

<210> SEQ ID NO 4
<211> LENGTH: 8
<212> TYPE: DNA
<213> ORGANISM: Escherichia coli
<220> FEATURE:
<223> OTHER INFORMATION: Description of Artificial Sequence:nucleic
      acid, double stranded, linear topology

<400> SEQUENCE: 4 agacgtct                                                                8

<210> SEQ ID NO 5
<211> LENGTH: 24
<212> TYPE: DNA
<213> ORGANISM: Escherichia coli
<220> FEATURE:
<223> OTHER INFORMATION: Description of Artificial Sequence:nucleic
      acid, double stranded, linear topology

<400> SEQUENCE: 5
tggaattgtg agcggataac aatt                                             24

<210> SEQ ID NO 6
<211> LENGTH: 4
<212> TYPE: DNA
<213> ORGANISM: Drosophila melanogaster
<220> FEATURE:
<223> OTHER INFORMATION: Description of Artificial Sequence:nucleic
      acid, double stranded, linear topology

<400> SEQUENCE: 6

-continued

```
taat                                                             4

<210> SEQ ID NO 7
<211> LENGTH: 9
<212> TYPE: DNA
<213> ORGANISM: MAT alpha 2 yeast
<220> FEATURE:
<223> OTHER INFORMATION: Description of Artificial Sequence:nucleic
      acid, double stranded, linear topology

<400> SEQUENCE: 7 catgtaatt                                                        9

<210> SEQ ID NO 8
<211> LENGTH: 13
<212> TYPE: DNA
<213> ORGANISM: Escherichia coli
<220> FEATURE:
<223> OTHER INFORMATION: Description of Artificial Sequence:nucleic
      acid, double stranded, linear topology

<400> SEQUENCE: 8
aaaagtgtga cat                                                  13

<210> SEQ ID NO 9
<211> LENGTH: 11
<212> TYPE: DNA
<213> ORGANISM: GAL4 yeast
<220> FEATURE:
<223> OTHER INFORMATION: Description of Artificial Sequence:nucleic
      acid, double stranded, linear topology

<400> SEQUENCE: 9
ccggaggaca g                                                    11

<210> SEQ ID NO 10
<211> LENGTH: 12
<212> TYPE: DNA
<213> ORGANISM: Papillomavirus sylvilagi
<220> FEATURE:
<223> OTHER INFORMATION: Description of Artificial Sequence:nucleic
      acid, double stranded, linear topology

<400> SEQUENCE: 10
accgacgtcg gt                                                   12

<210> SEQ ID NO 11
<211> LENGTH: 6
<212> TYPE: DNA
<213> ORGANISM: GCN4 yeast
<220> FEATURE:
<223> OTHER INFORMATION: Description of Artificial Sequence:nucleic
      acid, double stranded, linear topology

<400> SEQUENCE: 11 atgatc                                                           6

<210> SEQ ID NO 12
<211> LENGTH: 9
<212> TYPE: DNA
<213> ORGANISM: zif268 murine
<220> FEATURE:
<223> OTHER INFORMATION: Description of Artificial Sequence:nucleic
      acid, double stranded, linear topology

<400> SEQUENCE: 12
```

```
-continued gcgtgggcg                                                                    9

<210> SEQ ID NO 13
<211> LENGTH: 9
<212> TYPE: DNA
<213> ORGANISM: human glucocorticoid
<220> FEATURE:
<223> OTHER INFORMATION: Description of Artificial Sequence:nucleic
      acid, double stranded, linear topology

<400> SEQUENCE: 13 cagaacatc                                                                    9

<210> SEQ ID NO 14
<211> LENGTH: 8
<212> TYPE: DNA
<213> ORGANISM: tfiid
<220> FEATURE:
<223> OTHER INFORMATION: Description of Artificial Sequence:nucleic
      acid, double stranded, linear topology

<400> SEQUENCE: 14 tatataaa                                                                     8

<210> SEQ ID NO 15
<211> LENGTH: 319
<212> TYPE: DNA
<213> ORGANISM: murine leukemia virus
<220> FEATURE:
<223> OTHER INFORMATION: Description of Artificial Sequence:nucleic
      acid, single stranded, linear topology

<400> SEQUENCE: 15
gaacagatgg aacagctgaa tatgggccaa acaggatatc tgtggtaagc agttcctgcc           60
ccggctcagg gccaagaaca gatggaacag ctgaatatgg gccaaacagg atatctgtgg          120
taagcagttc ctgccccggc tcagggccaa gaacagatgg tccccagatg cggtccagcc          180
ctcagcagtt tctagagaac catcagatgt ttccagggtg ccccaaggac ctgaaatgac          240
cctgtgcctt atttgaacta accaatcagt tcgcttctcg cttctgttcg cgcgcttctg          300
ctccccgagc tcaataaaa                                                       319

<210> SEQ ID NO 16
<211> LENGTH: 319
<212> TYPE: DNA
<213> ORGANISM: murine leukemia virus
<220> FEATURE:
<223> OTHER INFORMATION: Description of Artificial Sequence:nucleic
      acid, single stranded, linear topology

<400> SEQUENCE: 16
acgcttgatc cggctacctg cccattcgac caccaagcga acatcgcat cgagcgagca            60 cgtactcgga tggaagccgg tcttgtcgat caggatgatc tggacgaaga gcatcagggg         120
ctcgcgccag ccgaactgtt cgccaggctc aaggcgcgca tgcccgacgg cgaggatctc         180
gtcgtgactt tctagagaac catcagatgt ttccagggtg ccccaaggac ctgaaatgac         240
cctgtgcctt atttgaacta accggtcagt tcgcttctcg cttctgttcg cgcgcttctg         300
ctccccgagc tcagctgcg                                                      319
```

INDEPENDENT HELPER VIRUS PACKAGING CELL LINE FOR PROPAGATING VIRAL VECTORS

CROSS-REFERENCE TO OTHER RELATED APPLICATIONS

This application is a divisional of U.S. application Ser. No. 08/822,963, filed on Mar. 21, 1997 now abandoned.

FIELD OF THE INVENTION

This invention relates to the field of recombinant nucleic acid technology, and more particularly, to the production of gene expression systems involving novel vectors and viral vectors as well as unique packaging cell lines for propagating such vectors or viral vectors and to the processes for producing them.

All patents, patent applications, patent publications, scientific articles, and the like, cited or identified in this application are hereby incorporated by reference in their entirety in order to describe more fully the state of the art to which the present invention pertains.

BACKGROUND OF THE INVENTION

Virus and nucleic acid vectors provide a means to deliver nucleic acid sequences to cells, and they are widely used in gene therapy applications. Critical to effective gene therapy is the ability to establish efficient expression of an Exogenous Nucleic Acid(s) in the target cell. Expression of exogenous nucleic acid in target cells can take place when the Exogenous Nucleic Acid(s) is/are either in an integrated or in an episomal state. Although expression in the episomal state can take place in target cells, expression in most cases persists for only limited periods of time. In contrast, the expression of Exogenous Nucleic Acids in an integrated state can be maintained for much longer periods.

Certain viruses have been of particular interest for use as vectors in gene therapy because of their ability to efficiently transfer and/or establish stable expression of Exogenous Nucleic Acid in the target cell. Although each particular family of virus may possess elements that confer specific advantages for development into a virus vector, each virus family also contains inherent features that limit its use as a viable means of human gene transfer.

Retroviruses have been a focus for development into virus vectors because they can establish stable integration of viral sequences. Current retroviral vectors can be produced from packaging cells in which the gag, pol and env elements are provided in trans through a plasmid or mutated virus. These vectors can transduce sequences of up to 7.5 to 8.0 kilobases. Nevertheless, several intrinsic features of retroviruses have hindered their use as virus vectors, and efforts to modify them to produce safe and efficient vectors have led to low yields of virus vector or to the inefficient expression of the exogenous gene in the target cell. [Morgenstern, J. P. and Land, Hartmut *Methods in Molecular Biology*, Vol. 7: Gene Transfer and Expression Protocols, 1991, edited by: E. J. Murray The Humana Press Inc., Clifton, N.J.; Anderson, W F *Science* 256:808-813 (1992); Mulligan, R C *Science* 260:926-932 (19931]; Smith, A E, Ann Rev. Microbiol. 49:807-838: Muzyczka, N., Curr. Top. Microbiol. Immunol. 158:97-129 (1992); Kotin, R. M., Human Gene Ther. 5:793-801 (1994); and Berliner, K. L., Curr. Top. Microbiol. Immunol. 158:39-66 (1992)). The contents of the foregoing book and publications are incorporated herein by reference. For example, it has been demonstrated that in retrovirus vectors the level of expression directed by an internal promoter/enhancer can be suppressed up to 50-fold by the flanking LTRs, presumably as a result of interference between transcriptional regulatory units. [*Methods in Molecular Biology, Vol. 7: Gene Transfer and Expression Protocols* Edited by: E. J. Murray The Humana Press, Inc. Clifton, N.J. (1991), supra; Emerman, M. and Temin, H. M., *Cell* 39:459-467 (1984); Emerman, M. and Temin, H. M., *Mol. Cell. Bio.* 6:792-800 (1986); Emerman, M. and Temin, H. M., *Nucleic Acids Res.* 14:9381-9396 (1986)]. The foregoing book and publications are also incorporated herein by reference. Attempts to overcome this suppression and achieve maximum expression of the exogenous nucleic acid have been made by deletion of the promoter and enhancer sequences within the U3 region of the 3' LTR in the provirus [Yu, S. F. et al. *Proc. Natl. Acad. Sci. USA* 83:3194-3198 (1986); Hawley, R. G. et al. *Proc. Natl. Acad. Sci. USA* 84:2406-2410 (1987); Yee, J. K. et al. *Proc. Natl. Acad. Sci. USA* 84:5197-5201 (1987)]. All of the foregoing publications are incorporated by reference into this application. Because the U3 region contains a polyadenylation signal, any deletions within this region can eliminate processing of nascent mRNA. In the absence of 3' RNA processing, such as polyadenylation, newly transcribed mRNA is highly unstable and, therefore, subject to immediate degradation. This accounts for the observation that provirus mRNA was not detectable in a packaging cell line transfected with retrovirus DNA possessing such a deletion (Dougherty, J. P. and Temin, H. M., *Proc. Natl. Acad. Sci. USA* 84:1197-1201 [1987], incorporated herein by reference). Addition of an exogenous SV40 polyadenylation signal to a site downstream from the 3' LTR has been used in an attempt to increase the virus mRNA level in the packaging cells. Several problems arise from the use of this method. The exogenous polyadenylation signal results in a lengthened viral mRNA with additional U5 and SV40 polyadenylation signal sequences which are not present in the retrovirus vector RNA in the packaging cells and in the target cells. This extra sequence can not only sterically hinder both the intermolecular and intramolecular transfer of templates during reverse transcription of the viral vector RNA, but can also decrease the packaging efficiency and the size of the exogenous nucleic acid sequence which can be inserted into the virus vector due to the size restriction of the RNA which can be packaged (Whitcomb, J. M. and Hughes, S. H. [1992] Ann. Rev. Cell Biol. 8:275-306, incorporated herein by reference). In cases where reverse transcription does occur, the exogenous polyadenylation signal is lost during the process of reverse transcription and it cannot be used for polyadenylation of mRNA transcribed from an internal gene which does not contain its own polyadenylation signal.

Virus vectors such as retroviruses that can randomly integrate into a cell genome have the potential to disrupt the structure and function of cell genes. The transcriptional elements within such a randomly integrated virus vector can activate potentially harmful genes such as oncogenes or genes triggering programmed cell death [Jaenisch, R., Harbers, K, Schnieke, A et al., Cell 32:209-216 (1983); Fung, Y. T. et al., Proc. Natl. Acad. Sci. USA 78:3412-3422 (1981); Neel, B. G. et al.; Cell 23:323-334 (1981); Payne, G. S. et al. Cell 23:311-322 (1983); Lewin, B., Genes V, Oxford University Press, New York (1994)]. The last-mentioned book and the foregoing publications are incorporated herein by reference. While removal of the transcriptional activity of the LTRs can reduce or eliminate the risk of unwanted gene activation by the integrated virus vector, the promoters/enhancers of the exogenous nucleic acid can still act to activate cellular genes near the site of integration.

Whereas certain viruses possess useful properties for gene transfer, their use is limited by the requirement for a helper virus or by an inability to provide for stable transfer of Exogenous Nucleic Acid to a target cell. For example, certain defective viruses can be propagated in packaging cells that provide the required packaging components but with the requirement for use of a helper virus. In order to insure safe use of such a virus vector preparation, however, the contaminating helper virus must be removed and the virus vector product must be extensively safety tested for the presence of any contaminating helper virus. The present invention overcomes these limitations by providing compositions for virus metamorphosis which can be used for propagation of virus vectors without the requirement of a helper virus.

The ability of a virus vector to integrate into the host genome provides distinct advantages for establishing stable expression of Exogenous Nucleic Acid in a target cell. The ability to integrate at specific sites is of further advantage by providing for a reduced possibility for an integrated vector to alter the structure and function of cellular genes. Unlike integrating viruses such as retroviruses, however, adeno-associated virus (AAV) is a virus that has been demonstrated to be able to integrate into a specific region of a cell genome, namely the q13-ter region of human chromosome 19 [Samulski, R. J. et al. EMBO Journal (1991); Kotin, R. M. et al., Genomics 10:831-834 (1991), the contents of both publications incorporated herein by reference]. This specific integration is directed by the AAV inverted terminal repeats and the Rep function [(Kotin et al., Proc. Natl. Acad. Sci. USA 87:2211-2215 (1990), incorporated herein by reference]. While such specific integration makes AAV an attractive candidate for use as a virus vector, existing AAV vectors cannot integrate at specific sites in a target cell genome. Other features that hinder the use of AAV vectors for gene therapy are the size restriction of the internal gene, the difficulty in growing virus in large amounts and the risk of helper-virus free contamination, all of which stem from the intrinsic mechanism of AAV replication.

By incorporating from different viruses the viral elements that mediate replication, virus vectors that derive specific advantages from each virus can be created to overcome the limitations associated with each virus vector. For example, the transfer of site-specific integration function from AAV into other virus vector systems can provide for such properties in a virus vector that may have useful properties for gene transfer but lacking any ability to integrate.

For gene delivery purposes, a virus vector can be developed from a virus that is native to a target cell or from a virus that is non-native to a target cell. In general, it is desirable to use a non-native virus vector rather than a native virus vector. While native virus vectors may possess a natural affinity for target cells, such viruses pose a greater hazard since they possess a greater potential for propagation in target cells. In this regard, animal virus vectors, wherein they are not naturally designed for propagation in human cells, can be useful for gene delivery to human cells. In order to obtain sufficient yields of such animal virus vectors for use in gene delivery, however, it is necessary to carry out production in a native animal packaging cell. Virus vectors produced in this way, however, normally lack any components either as part of the envelope or as part of the capsid that can provide tropism for human cells. For example, current practices for the production of non-human virus vectors, such as ecotropic mouse (murine) retroviruses like MMLV, are produced in a mouse packaging cell line. Another component required for human cell tropism must be provided.

While non-viral nucleic acid complexes can provide significant advantages for gene delivery, these advantages have not or cannot be realized by the use of non-viral nucleic acid complexes that rely on non-specific binding components. The present invention overcomes these limitations by providing for specific complex formation between nucleic acid and protein components wherein the binding of protein molecules that provide useful properties for gene transfer can be localized to defined regions of the nucleic acid construct. Such localization of specific binding proteins in the nucleic acid constructs can reduce or eliminate any interference with the region segments in the constructs that are involved in or provide for biological activity. The present invention also provides for the controlled displacement of such specific binding proteins from their cognate binding sites wherein such displacement can remove any possible interference with biological function or can release proteins that can provide useful function in the cell.

SUMMARY OF THE INVENTION

The present invention provides novel vectors and viral vectors for use in systems for delivering and expressing desired genes and gene sequences. One such novel vector is shown to be capable of expressing an exogenous gene or exogenous nucleic acid sequences in a target cell of interest. The vector comprises a viral vector, a viral vector nucleic acid, or a nucleic acid construct that comprises a viral vector nucleic acid sequence. The vector comprises the following nucleic acid component or components: i) one or more native promoter/enhancer regions in which at least one sequence segment has been modified, (ii) one or more non-native promoter/enhancers or a non-native promoter's gene or gene segment, and (iii) a native viral vector terminator or a processing signal or segment thereof, or both.

The present invention also provides a novel viral vector comprising a virus or viral portion having at least two adsorbing components on the surfaces or envelopes thereof. One adsorbing component is directed to a packaging cell line for the vector, and the other adsorbing component is for adsorbing to a target cell for delivering the vector.

Further provided by this invention is a novel viral vector comprising a virus or viral portion thereof in which at least two components on the surfaces or envelopes are found. The first component is native to the virus while the second component is generally characterized as being non-native to the viral vector, and further, being capable of adsorption to a target cell of interest, while being incapable of adsorption to a cell native for the same viral vector.

The present invention provides yet further a novel vector selected from the following group: a (i) viral vector, (ii) a viral nucleic acid, and (iii) a nucleic acid construct. The vector comprises a non-native nucleic acid sequence coding for a segment, the segment being capable of integrating into a target cell's genome, and the vector itself being capable of producing or introducing a first nucleic acid in the target cell. With respect to the first nucleic acid, it is itself capable of producing a second nucleic acid that comprises a portion of the first nucleic acid. The second nucleic acid comprises the integration segment and is itself capable of expressing an exogenous gene or an exogenous nucleic acid sequence as the case may be.

Also provided by this invention is a novel first vector selected from the group consisting of (i) a viral vector comprising a viral nucleic acid and a viral vector packaging component or components, (ii) a viral nucleic acid, and (iii) a nucleic acid construct. When introduced into a packaging cell, the first vector is capable of producing a second vector selected from the group consisting of (a) a second viral vector, b) a viral nucleic acid, and (c) a second nucleic acid construct, each of which group members are capable of expressing an exogenous gene or exogenous nucleic acid sequence in a target cell of interest. The first vector is capable of producing the second vector in the packaging cell, and the packaging cell is capable of providing one or more packaging components for the second viral nucleic acid. In this unique vector, the second viral nucleic acid or the second nucleic acid construct is structurally different from the first (i) viral nucleic acid or the first (iii) nucleic acid construct. Alternatively, more than one packaging component for the second viral vector may be different from the first viral vector packaging component or components (ii). As a further alternative, both kinds or sets of structural differences may be present in the same vector. That is to say, the second viral nucleic acid or the second nucleic acid construct may be different from the first, and/or the packaging components for the second may be different from the first.

This invention is also directed to novel packaging cell lines for propagating any of the foregoing vectors or viral vectors, including the last-mentioned first vector. Thus, the packaging cell line of the present invention provides at least two packaging components for the surface or envelope of the viral vector. Other packaging cell lines for propagating other viral vectors are also provided. In these, the cell line is non-native to the viral vector component or components but native to the viral vector nucleic acid. The packaging cell line expresses one or more adsorbing components on its membrane or surface. Such adsorbing components are for adsorption to the non-native component of the vector and broadly comprise receptor(s) or binding partner(s).

Processes for producing any of the novel viral vectors or viral vector nucleic acid of this invention are also contemplated and provided in this disclosure. In these processes, the desired vector is introduced into an appropriate packaging cell under conditions sufficient or appropriate to produce the viral vector or viral vector nucleic acid.

Still yet provided by this invention are novel and unique packaging cell lines for propagating viral vectors independent of helper viruses. In such packaging cell lines, the viral vector comprises a nucleic acid component and a non-nucleic acid component. The sequence or sequences for the viral vector nucleic acid component is stably integrated in the genome of the cell line. The sequence or sequences for the non-nucleic acid component of the viral vector are introduced into the packaging cell line by various means. These means can involve transient expression, episomal expression, stable integration expression, or any combination of such foregoing means.

BRIEF DESCRIPTION OF THE FIGURES

FIG. 2 shows the wild type 3' LTR native sequence that was removed from the plasmid pENZ1 as well as the non-native modified 3' LTR sequence that replaced it (SEQ ID NO:15 and 16). The modified sequences are designated by bold italics.

DETAILED DESCRIPTION OF THE INVENTION

Figure 1:
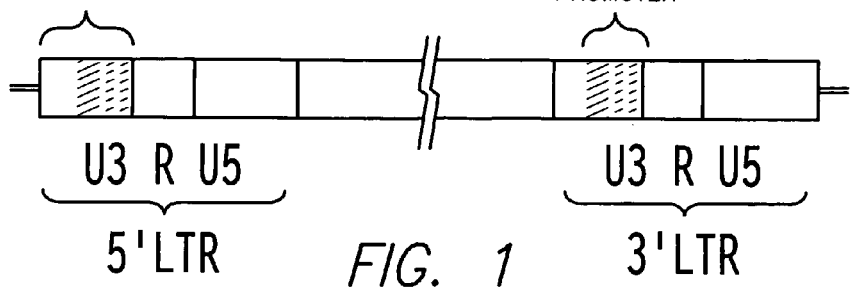
FIG. 1 depicts the general replacement strategy to a retroviral vector sequence present in the plasmid pENZ1.

The definitions below are useful to an understanding of the present invention and this disclosure.

DEFINITIONS

Heterologous Vector: A virus vector or non-virus vector, including non-viral specific complex that consists of at least one Non-Native Vector Component and that is capable of delivering an Exogenous Nucleic Acid to a cell and which can facilitate Exogenous Nucleic Acid expression in a cell. The Heterologous Vector contains a functional native segment or segments that interfere with the expression of an exogenous gene or an exogenous nucleic acid. The native segment or segments have been modified wherein the interference is reduced or eliminated and/or native termination/RNA processing is retained.

Non-Native Vector Component: A nucleic acid sequence derived from any biological system, or an altered or modified native element, that forms a components) of a Heterologous Vector. The components) function in or mediate directly or indirectly in a cis or trans fashion either in vivo or in vitro to provide or effectuate 1) expression (including termination signal) of the Exogenous Gene or Exogenous Nucleic Acid of the Heterologous Vector in a target cell of interest; 2) integration; and 3) propagation, yield and assembly.

Expression Cassette (or the expression of exogenous nucleic acid sequence or exogenous gene): A nucleic acid sequence that contains all the elements required for exogenous gene expression or the expression of an exogenous nucleic acid sequence or segment, and that is inserted into a vector for the purpose of expression in a target cell of interest. Such elements embrace both native and non-native vector components or combinations thereof, including modified or unmodified promoter/enhancer sequences for the expression of Exogenous Nucleic Acid or Exogenous Gene that may contain a gene or gene segment corresponding to the non-native promoter/enhancer, modified or native viral promoter/enhancers and signals for termination, RNA processing, polyadenylation and RNA transport.

cis effect: The effect exerted by one functional segment of a vector nucleic acid on the function of another distal sequence of vector nucleic acid.

Heterologous Virus Vectors

The present invention provides compositions and methods of use for Heterologous Vectors that have useful properties for gene delivery to cells, i.e., 1) efficient propagation in a packaging cell and 2) the safe and efficient expression of Exogenous Nucleic Acid in a cell. These benefits are achieved by the use of Non-Native Vector Components that can provide one or more such properties to a virus vector.

Expression of Exogenous Nucleic Acid in a virus vector can in many cases be inefficient because of the virus vector native promoters/enhancers activity that interferes: with the function of non-native promoters/enhancers driving Exogenous Nucleic Acid expression (Emmerman and Temin, 1986, contents of which are incorporated herein by reference). Efforts to eliminate this interference by deletion of the virus vector native promoters/enhancers produce cis effects that occur at sites distal to the modification site. Such cis effects may lead to loss or reduction in termination and/or RNA processing which causes reduction or a diminishment in the expression of Exogenous Nucleic Acid as well as greatly reduced or an altogether eliminated ability to propagate efficiently in a packaging cell. The addition of a non-native polyadenylation signal to a site downstream from the 3' LTR has been used in an attempt to restore the lost function (Dougherty and Temin, 1987, incorporated herein by reference). Such an approach is limited in several critical aspects. This exogenous polyadenylation signal results in a lengthened viral mRNA with additional U5 and SV40 polyadenylation signal sequences which are not present in the retrovirus vector RNA in the packaging cells and in the target cells. This extra sequence can not only sterically hinder both the intermolecular and intramolecular transfer of templates during reverse transcription of the viral vector RNA, but it can also decrease the packaging efficiency and the size of the exogenous nucleic acid sequence which can be inserted into the virus vector due to the size restriction of the RNA which can be packaged (Whitcomb and Hughes, 1992, incorporated herein by reference). In cases where reverse transcription does occur, the exogenous polyadenylation signal is lost during the process of reverse transcription and it cannot be used for polyadenylation of mRNA transcribed from an exogenous gene which does not contain its own polyadenylation signal.

It is another aspect of this invention to overcome the above limitations in the art by providing modification in the natural promoters/enhancers segment through a variety of means including substitution, addition, mutation or any combination thereof. The present invention overcomes these limitations by providing in one feature the artificial reconstitution of the native promoters/enhancers segment of the vector which has been demonstrated to reduce or eliminate such cis effects in the vector. This reconstitution or modification is carried out in accordance with this invention, for example, through the replacement of Heterologous Vector nucleic acid sequences with Non-Native Vector Components that can provide such restoration or even improvement of vector virus functions. This reconstitution can be accomplished by replacement of virus vector promoter and/or enhancer sequences with Non-Native Vector Components to provide a virus vector with an mutated LTR in which the native promoter/enhancer function is inactivated in such a manner that eliminates interference with non-native promoter/enhancer functions. In this case, the virus vector retains fully active native termination functions and native RNA processing functions for expression of virus vector RNA in a packaging cell and for expression of Exogenous Nucleic Acid in a target cell.

Thus, the present invention provides a vector comprising a viral vector, a viral vector nucleic acid, or a nucleic acid construct that comprises a viral vector nucleic acid sequence. The vector is capable of expressing an exogenous gene or exogenous nucleic acid sequences in a target cell of interest, the vector comprising a nucleic acid component or components. The latter nucleic acid component or components comprise (i) one or more native promoter/enhancer regions in which at least one sequence segment has been modified, (ii) one or more non-native promoter/enhancers or a non-native promoter's gene or gene segment, and (iii) a native viral vector terminator or a processing signal or segment thereof, or both. Additionally, the aforementioned viral vector further comprises a non-native terminator or two or more modified sequence segments.

Such modifications may take various forms. For example, a native sequence segment can be substituted by a non-native sequence segment in the one or more promoter/enhancer regions of the vector. Further, the substitution can be of approximately the same size. In another aspect, the modification can comprise a mutation selected from any of the group members represented by a point mutation, a deletion, an insertion, and a substitution, or a combination of any of the foregoing.

In one preferred aspect, the viral vector is a retrovirus. In another, the terminator, or processing signal, or both, as the case may be, can include a polyadenylation signal. In addition, such a viral vector can comprise a segment of the viral vector terminator or a segment of the processing signal, or both. Additionally, the function of the one or more promoter/enhancers will have been reduced, inhibited or eliminated in the present viral vector.

With respect to the one or more non-native promoters, these are capable of producing an RNA lacking a polyadenylation signal. A number of non-native promoters can be used in accordance with this invention. Simply by way of example, such non-native promoters can be selected from the group of genes represented by or designated as snRNA, tRNA, and rRNA, or a combination of any of the foregoing.

In another aspect of this invention, the afore-described viral vector further comprises one or more gene or gene segment sequences of the snRNA, tRNA or rRNA gene or genes. The snRNAs are well described in the literature, and these include, for example, any of the members selected from the group consisting of U1, U2, U3, U4, U5, U6, U7, U8, U9, U10 and U11, or a combination of any of the foregoing.

It should also be pointed out that in the viral vector described above, one or more non-native promoters gene or gene segment sequence can or will have been modified. Such modifications can also take a number of forms, including the substitution or replacement of or addition to the one or more non-native promoter's gene sequence with the exogenous gene or an exogenous nucleic acid sequence.

Non-Native Vector Components useful for these purposes include non-native nucleic acid sequences in the vector. Such nucleic acid sequences can be derived from any biological system or can be chemically synthesized or can be prepared by recombinant DNA methods or by any combination of such methods, Such sequences can be approximately the same size as the vector virus sequences that are replaced. Thus, such sequences can range in size from approximately 2 to approximately 188 bases or base pairs in length, or longer. Such sequences can be used to replace one or more sequences in such regions of the virus vector as promoter and/or enhancer sequences, or any other native sequences in which its ability leads to cis effects. Such replacements can be carried out by the conventional methods of recombinant DNA (see Sambrook, J., Fritsch, E. F. and Maniatis, T. Molecular Cloning, 2nd ed. Cold Spring Laboratory, Cold Spring Harbor, N.Y., 1989, the contents of which textbook are incorporated herein by reference), and they can be conveniently performed on virus vector nucleic acid genomes or fragments thereof that are present as double stranded DNA in plasmids.

Modifications to provide reconstitution of cis effects in such vectors as retroviruses can, for example, be accomplished by replacements in the U3 region of the 3' LTR region of a retrovirus vector genome present in a plasmid, i.e., a vector nucleic acid construct. The propagation of retrovirus vectors can proceed by introduction of such a plasmid into a packaging cell wherein transcripts of the virus vector genome are produced and reverse transcribed after transduction into a target cell. As a result of these processes, modifications made to the 3' LTR in a vector plasmid will be present in the 5' LTR of propagated retrovirus vectors.

Reconstitution has been accomplished according to the teachings of this invention in a retrovirus vector provirus DNA contained in a vector plasmid (designated pENZ-1) by modifications of the 3' LTR. Three separate sequences from the promoter/enhancer region were replaced with non-native sequences of approximately the same size. A sequence of 188 base pairs from the enhancer region of the 3' LTR was replaced with an unrelated sequence of 188 base pairs derived from the bacterial neo gene. Two separate sequences in the promoter region, one of 2 bases and the other of 6 bases, were also replaced with nucleic acid segments of the same size. Introduction of this provirus DNA construct into a packaging cell (either GP+E-86 or PA 317) produced retrovirus vectors at titers of up to $10^6$ as measured by transduction of G418 resistance. This is illustrated in FIGS. 1 and 2.

Thus, the present invention also provides a first vector selected from the group consisting of (i) a viral vector comprising a viral nucleic acid and a viral vector packaging component or components, (ii) a viral nucleic acid, and (iii) a nucleic acid construct, wherein when introduced into a packaging cell, the first vector is capable of producing a second vector selected from the group consisting of (a) a second viral vector, (b) a viral nucleic acid, and (c) a second nucleic acid construct, each being capable of expressing an exogenous gene or exogenous nucleic acid sequence in a target cell of interest. The first vector is capable of producing in the packaging cell the second vector, and the packaging cell is capable of providing one or more packaging components for the second viral nucleic acid. The second viral nucleic acid or the second nucleic acid construct is structurally different from the first (i) viral nucleic acid or the first (iii) nucleic acid construct, or more than one packaging component for the second viral vector is different from the first viral vector packaging component or components (ii), or both instances of structural differences may be present in this first vector. In one aspect, the first vector comprises a retrovirus and the second vector comprises adeno-associated virus (AAV).

With respect to these aforementioned structural differences, these comprise or take on any number of forms, including any differences that are selected from the following group members: the nucleic acid chemical nature, the nucleic acid form, the nucleic acid size, and functional elements, or a combination of any of the foregoing. With respect to the nucleic acid chemical nature, the second viral nucleic acid or the second nucleic acid is selected from any of the group members consisting of or designated as RNA and DNA, and the (i) viral nucleic acid or the (iii) nucleic acid construct comprises a different member of the group to impart a structural difference between the elements. With respect to the nucleic acid form, the second viral nucleic acid or the second nucleic acid is selected from any of the group members consisting of single-stranded, double-stranded and partially double-stranded, and the (i) viral nucleic acid or the (iii) nucleic acid construct comprises a different member of the group to impart a structural difference therebetween. With respect to the nucleic acid size, the second viral nucleic acid or the second nucleic acid comprises a segment of the (i) viral nucleic acid or the (iii) nucleic acid construct. With respect to the functional elements, the second viral nucleic acid or the second nucleic acid comprises one or more promoters, one or more enhancer regions, an integration segment and a terminator, or a portion or a segment or a combination of any of the foregoing, and the (i) viral nucleic acid or the (iii) nucleic acid construct comprises a different member of the group to impart a structural difference therebetween.

In preferred aspects of this invention, the first vector comprises a retrovirus and the second vector comprises adeno-associated virus. In other preferred aspects, the first vector comprises adeno-associated virus and the second vector comprises a retrovirus.

Retrovirus vectors can also be reconstituted with a nucleic acid sequence for a non-native promoter.

In comparison to a non-reconstituted modified retroviral vector that has exclusively lost its propagation capability, the reconstitution of cis effects, as described earlier, can thus provide virus vectors with a) the ability to express Exogenous Nucleic Acid at a maximum level, and/or b) the ability to propagate efficiently in a packaging cell. Furthermore, as a result of the inactivation of virus vector promoter/enhancer function, such Heterologous Vector viruses could have properties for safe use in a gene delivery system. For example, where said Heterologous Vector contains a non-native promoter which cannot direct the transcript of a polyadenylated RNA, then such a vector has a greatly reduced or lost ability to activate the expression of polyadenylated mRNA or non-polyadenylated mRNA from cellular genes that utilize either polymerase I-dependent, polymerase II-dependent or polymerase III-dependent promoters as a result of random integration of the vector. The present invention provides additional compositions for the safe use of Heterologous Vectors by the use of non-native promoters/enhancers for the expression of Exogenous Nucleic Acid wherein such promoters/enhancers lack the ability to provide poly(A) signal sequence for activating expression of polyadenylated mRNA. The use of such non-native promoters/enhancers for expression of Exogenous Nucleic Acid in such Heterologous Vectors can provide safe virus vectors in which the ability to activate polyadenylated mRNA synthesis of cellular genes by either virus vector native promoters/enhancers or by non-native promoters/enhancers is markedly reduced or eliminated.

Non-native elements in the vector that provide safe expression of Exogenous Nucleic Acid can be derived from any biological system and can include promoters/enhancers and compatible processing signals that do not direct the transcription of polyadenylated RNA. These promoters/enhancers include such elements that are recognized by RNA polymerase I, RNA polymerase II or RNA polymerase III that provide for the synthesis of cellular RNA elements such as ribosomal RNA, transfer RNAs, small nuclear RNAs such as U1, U2, U3, U4, U5, U6, U7, U8, U9. U10 and U11. These sequences of cellular RNA elements can be useful to the practice of this invention wherein they can be used to form chimeric RNA molecules with RNA sequences that can provide such biological functions as antisense regulation of gene expression, ribozyme activity, sense sequences for expression of an exogenous gene or exogenous nucleic acid, and the like.

Such sequences providing for biological activity can be incorporated into such a cellular RNA gene or gene segments by partial or complete replacement of some or all of the sequences of the cellular RNA gene or gene segments, or by the addition of such sequences to the RNA gene sequence. Using the methods of recombinant DNA, such chimeric molecules can be formed by utilizing the cloned sequences for the cellular RNA elements and coding sequence for RNA transcripts of exogenous gene or gene segments or exogenous nucleic acid. Such a chimera could be all or in part chemically synthesized. Nucleic acid sequences providing for the synthesis of such chimeric RNA molecules can be conveniently incorporated into double stranded Heterologous Vector DNA present in a plasmid by the methods of recombinant DNA as described above. Heterologous Vectors providing for expression of such RNA compositions are presented in FIGS. 5, 6 and 7.

For the use of such chimeras formed between a cellular RNA gene or gene segment and a sequence coding for an exogenous gene or exogenous nucleic acid, modifications of the cellular RNA gene may lead to enhanced function of the cassette. For example, in chimeric molecules formed between an antisense RNA and a U1snRNA, such modifications of the U1 snRNA that could provide a U1 snRNP complex with loss of catalytic function and/or loss of transport properties and/or loss of protein interaction could further the expression of antisense function in a cell. Modifications that could provide such properties could result from deletions, additions or from alterations of one or more bases of the sequence of such a molecule. Such a modified U1 system has been prepared from a U1 molecule containing an altered base sequence, i.e., a change of C to T at position 4 of the U1 RNA transcript present in plasmid pHSD-4 (Manser, T. and Gesteland, R., Cell 29:257-264 (1982), the contents of which are incorporated by reference). This U1 was used to form a chimeric molecules with each of three different antisense sequences, each directed against an HIV-1 target sequence. Replacement was done by replacement of a portion of the transcribed region of U1 (present in pHSD-4) with each antisense sequence.

Such chimeric molecules can be inserted into Heterologous Vectors such as retroviruses to provide for delivery to and expression of such chimeric antisense molecules in a target cell. The absence of any vector promoter activity and the lack of production of any peptide by the virus vector sequences or by the Exogenous Nucleic Acid thus produces no non-native protein in a target cell, thus eliminating the possibility for an immune response. See Roy-Chowdhury et al., "Novel Processes Implementing Selective Immune Down Regulation (SIDR)," U.S. patent application Ser. No. 08/808, 629 filed on Feb. 28, 1997, the contents of which are incorporated herein by reference).

Such immunogenically silent vectors could be especially useful for ex vivo gene transfer to such cells as hematopoietic stem cells. Treatment of virus infections of these cells could benefit from the use of these vectors for the delivery of biologically active RNAs such as antisense (including ribozymes) and sense RNAs directed against the infecting viruses. For example, treatment of diseases such as HIV-1 (and certain viral leukemias) could benefit from gene transfer of such sequences to hematopoietic stem cells as a means for providing a source of CD4+ cells with resistance to HIV-1 infection. Cells for this purpose could be derived from autologous sources such as the bone marrow or the circulating cells of the donor or from heterologous sources such as fetal cord blood. Such cells could be grown and transduced with such a vector according to procedures such as described by (Nolta et at. 1995 Blood 86.101-110; Xu et al., Blood 86:141-146 (1995); Bertolini et al., Cancer Research 56:2566-2572 (1996); and Wells et al., Gene Therapy 2:512-520 (1995)). The contents of the foregoing publications are incorporated herein by reference. These procedures could utilize autologous sera and stroma. Cells so treated could be administered to patients who had previously undergone partial or complete ablation.

Immunogenically silent Heterologous Vectors constituted as described above could also be utilized for in vivo gene delivery. Such tissues as liver, lung, kidney, brain, muscle, epithelial tissues and other tissues not easily amenable to ex vivo procedures could be targeted by the administration of such virus vectors to the bloodstream or by direct injection into a tissue or organ. Such treatment procedures can be used in combination with other methods.

Virus Metamorphosis

The present invention provides compositions and methods of use for vectors or viral vectors that can, in an appropriately constructed packaging cell or in a target cell, propagate to a virus vector nucleic acid or virus vector which differ from the original vector in various elements as described herein, or even a second virus vector, or produce a virus vector genome of a different or even second virus vector or produce a nucleic acid that substantially resembles the genome of a different or second virus vector. Such a process of virus metamorphosis can be mediated by a virus vector modified in its nucleic acid sequence by the incorporation of one or more non-native sequences. Introduction of such a modified nucleic acid component or components into an appropriately constructed packaging cell can provide propagation of such second virus vectors from the original vector, or its introduction into a target cell can produce a nucleic acid of a second virus vector or virus vector nucleic acid which contains properties other than found in the original vector, including integration into the target cell genome. Compositions are also provided for packaging cells that can be modified to provide virus metamorphosis by the incorporation of components non-native to said packaging cell. Compositions for virus metamorphosis can be useful for the production of defective virus vectors wherein such viruses can be propagated without the requirement for a helper virus and which can also be useful to provide properties for the integration of Exogenous Nucleic Acid into the genome of a target cell.

Whereas certain viruses possess useful properties for gene transfer, their use is limited by the requirement of a helper virus for virus vector production or by an inability to provide for stable transfer of Exogenous Nucleic Acid to a target cell or for integration of Exogenous Nucleic Acid at preferred sites of a target cell genome. For example, certain defective viruses can be propagated in packaging cells that provide the required packaging components but with the requirement for use of a helper virus. In order to insure safe use of such a virus vector preparation, however, the contaminating helper virus must be removed and the virus vector product must be extensively safety tested for the presence of any contaminating helper virus. The present invention overcomes these limitations by providing compositions for virus metamorphosis which can be used for propagation of second virus vectors without the requirement for a helper virus.

Among the novel and useful viral vectors of the present invention is one comprising a virus or viral portion having on a surface or an envelope thereof at least two adsorbing components, one component for adsorption to a packaging cell line for the vector, and the other component for adsorption to a target cell for delivery of the vector. Both aforementioned components can be native to the viral vector, or both can be non-native to the viral vector, or in some instances one component can be native and the other component can be non-native. When at least one component is native to the viral vector, one of the components can be ecotropic or amphotropic. Such non-native components are known in the art and can take a number of forms. These include, by way of example, any of the members selected or derived from the group consisting of Human Immunodeficiency Virus (HIV), Hepatitis B Virus (HBV), Hepatitis C Virus (HCV), Herpes Simplex Virus (HSV), and Vesticular Stomatis Virus (VSV), and a part or portion thereof, or a combination of any of the foregoing. In the case of HIV or its part or portion thereof, the non-native component can comprise gp120. In the case of HBV or HCV, the non-native component comprises a surface antigen. One or the other or both components of the viral vector can be selected from any of the members of the group consisting of a protein, an oligo- or polypeptide, a glycoprotein, a fused peptide, a recombinant peptide, a modified protein, or a combination of any of the foregoing.

In preferred aspects, the above described viral vector comprises a retrovirus such as a murine retrovirus.

Vectors that can provide for vector metamorphosis can also be used to provide integration properties to the vectors derived from the original vector. While certain viruses possess useful properties for gene delivery, their use is limited by an inability to integrate and/or to remain stably associated with a target cell, and such virus vectors can thus only provide for expression of Exogenous Nucleic Acid for a limited period. Compositions for virus metamorphosis can be used to provide for stable expression of Exogenous Nucleic Acid by providing properties for stable integration into a target cell genome of the second vector where the original vector lacks integration capability. Such properties can be provided to a vector or virus vector by components non-native to such a vector or virus vector wherein such properties can be derived from other viruses or from other biological systems or synthetically.

Virus metamorphosis can proceed in a packaging cell or in a target cell by the introduction into said cell of the nucleic acid of an initiating vector (or first virus vector) wherein said nucleic acid is a component of a virus vector, is a virus vector nucleic acid or is a nucleic acid construct or a component thereof. Propagation of said nucleic acid in a packaging cell or in a target cell can directly or indirectly yield a nucleic acid with properties native to a virus vector (second virus vector) that is unrelated to the first virus vector wherein the nucleic acid of the second virus vector differs from the nucleic acid of the first virus vector in i) complexity, wherein it can be shorter or longer, ii) in chemical nature wherein it can be either single or double stranded RNA or DNA or partially single stranded and partially double stranded RNA or DNA and iii) in the function of promoters/enhancers, integration sequences and termination, processing sequences, or the difference lies in packaging surface component or components. The properties of the second vector nucleic acid could provide for the packaging of the second vector in a packaging cell which is constructed to provide the required components for the second vector packaging. Alternatively, the nucleic acid of such an second virus vector so produced in a target cell could contain properties for its incorporation into the genome of said cell.

Virus vectors useful for the practice of this invention can be derived from plant, bacterial, animal and human viruses wherein these can be modified by components non-native to said initiating: vector virus. Such components can normally be derived from other viruses but could also be derived from other biological systems or made synthetically. Such components include but are not necessarily limited to nucleic acid sequences that provide for virus propagation, integration function and gene expression for virus components. These include the LTR sequences of retroviruses, the integrase protein of retroviruses, the reverse transcriptase of retroviruses, the ITR sequences of AAV, the rep genes of AAV, the cap genes of AAV and other components that can provide useful functions.

The nucleic acid sequences of virus vectors used to initiate virus metamorphosis, i.e., and first virus vector, can be conveniently constructed by the methods of recombinant DNA wherein the non-native vector components can be incorporated into a vector nucleic acid sequence.

Packaging cells for the practice of this invention can be prepared by the introduction of nucleic acid sequences normally derived from both the initiating vector and the second vector. Such nucleic acid sequences can provide for the synthesis of the second vector component(s) including packaging components, polymerases or other required enzymes, and for the synthesis of the second vector nucleic acid. Such nucleic acid sequences can present in such cells in either an integrated or in an episomal state.

Virus vectors that can be utilized for virus metamorphosis include retroviruses like the Moloney murine leukemia virus (MMLV). A retrovirus vector (vector, vector nucleic acid, or nucleic acid construct) can be modified to propagate an second virus vector, such as the AAV, by incorporating a sequence of the AAV ITR into the retroviral vector nucleic acid sequence. Two such sequences can be inserted into the retrovirus vector nucleic acid. Such vector can direct the synthesis of retrovirus vector RNA in a packaging cell and the packaging cell line can provide reverse transcriptase for synthesis of AAV DNA. Exogenous Nucleic Acid are present in the region flanked by the AAV ITRs. The retroviral vector nucleic acid can be further modified by inactivation of the ppt sequence segment function (or others), thus eliminating synthesis of the second DNA strand after reverse transcription as a means of providing single stranded DNA copies of the second vector (for example, AAV). This can be accomplished by deletion of the ppt sequence or by the replacement of the retroviral ppt sequence with one of the AAV ITR sequences or with an AAV rep sequence by methods described elsewhere in this patent. AAV rep and cap nucleic acid sequences can be provided to packaging cells as part of the retrovirus nucleic acid component or such sequences can be provided separately on plasmids or other nucleic acid entities either inserted into a cell genome or present in the packaging cell in an episomal state or in a transient state. This invention further provides a viral vector comprising a virus or viral portion thereof having on a surface or an envelope at least two components, the first component being native to the virus, and the second component characterized by three characteristics. First, it is non-native to said viral vector. Second, it is capable of adsorption to a target cell of interest. Third, the second component is incapable of adsorption to a cell native for the viral vector. In a preferred aspect, the viral vectors is a retrovirus. Suitable or appropriate retroviruses have been well characterized in the literature and can take a number of diverse forms. Merely by way of example, such retroviruses can be selected from any of the members of the group consisting of a murine leukemia virus, a human immunodeficiency virus, a human T cell leukemia virus and a Gibbon ape leukemia virus, or a combination of any of the foregoing.

The non-native component in the above-described viral vector can also take a number of forms, all of which are well described in the literature. These include any or all of the following members selected or derived from the group consisting of Human Immunodeficiency Virus (HIV), Hepatitis B Virus (HBV), Hepatitis C Virus (HCV), Herpes Simplex Virus (HSV), and Vesticular Stomatis Virus (VSV), and a part or portion thereof, or a combination of any of the foregoing. In the case of HIV, the derived member can comprise gp120. In another instance, the non-native component can comprise HBV or HCV surface antigen.

The present invention contemplates a number of useful target cells, including any of the members selected from the group consisting of T cells, liver cells, bone marrow cells and epithelial cells, or a combination of any of the foregoing.

The present invention also provides a vector selected from the group consisting of a (i) viral vector, (ii) a viral nucleic acid, and (iii) a nucleic acid construct, the vector comprising a non-native nucleic acid sequence coding for a segment, the segment being capable of integration into a target cell's genome, and the vector being capable of producing or introducing a first nucleic acid in the target cell, the first nucleic acid being capable of producing a second nucleic acid that comprises a portion of the first nucleic acid, the second nucleic acid comprising the integration segment and being capable of expressing an exogenous gene or an exogenous nucleic acid sequence. In one aspect, this vector can comprise a viral vector and the integration segment can be non-native to the viral vector. The vector can also comprise a viral nucleic acid and the integration segment can also be non-native to the viral vector. In one preferred embodiment, the viral vector comprises adenovirus. In another, the first nucleic acid comprises a retrovirus and the second nucleic acid comprises adeno-associated virus (AAV). In yet another, the first nucleic acid comprises AAV and the second nucleic acid comprises a retrovirus. Still further, the second nucleic acid sequence comprises retroviral LTR or AAV.

This invention also provides a process for producing any of the viral vectors or viral vector nucleic acids as disclosed herein or claimed below. Such a process typically comprises the steps of providing such vector and introducing it into a packaging cell under conditions to produce the viral vector or said viral vector nucleic acid. In one aspect, the nucleic acid construct can be been modified in a promoter/enhancer region, in a non-native promoter. In other aspects of the just described process, the nucleic acid construct is capable of stable integration into the genome of said packaging cell line. It should not be overlooked that in the case where a nucleic acid construct is employed in such process, the construct can be modified by means of an episome or by means of transient expression.

This invention also provides a packaging cell line for propagating a viral vector independent of a helper virus. The viral vector can comprise a nucleic acid component and a non-nucleic acid component. The sequence or sequences for the viral vector nucleic acid component can be stably integrated in the genome of the cell line, and the sequence or sequences for the non-nucleic acid component of the viral vector are introduced into the packaging cell line by a means selected from the group consisting of transient expression, episomal expression, stably integrated expression, or a combination of any of the foregoing.

Packaging cells for this purpose can be prepared to contain retroviral reverse transcriptase sequences in order to provide for reverse transcription of transcripts produced from the initiating vector (retrovirus).

Figure 8:
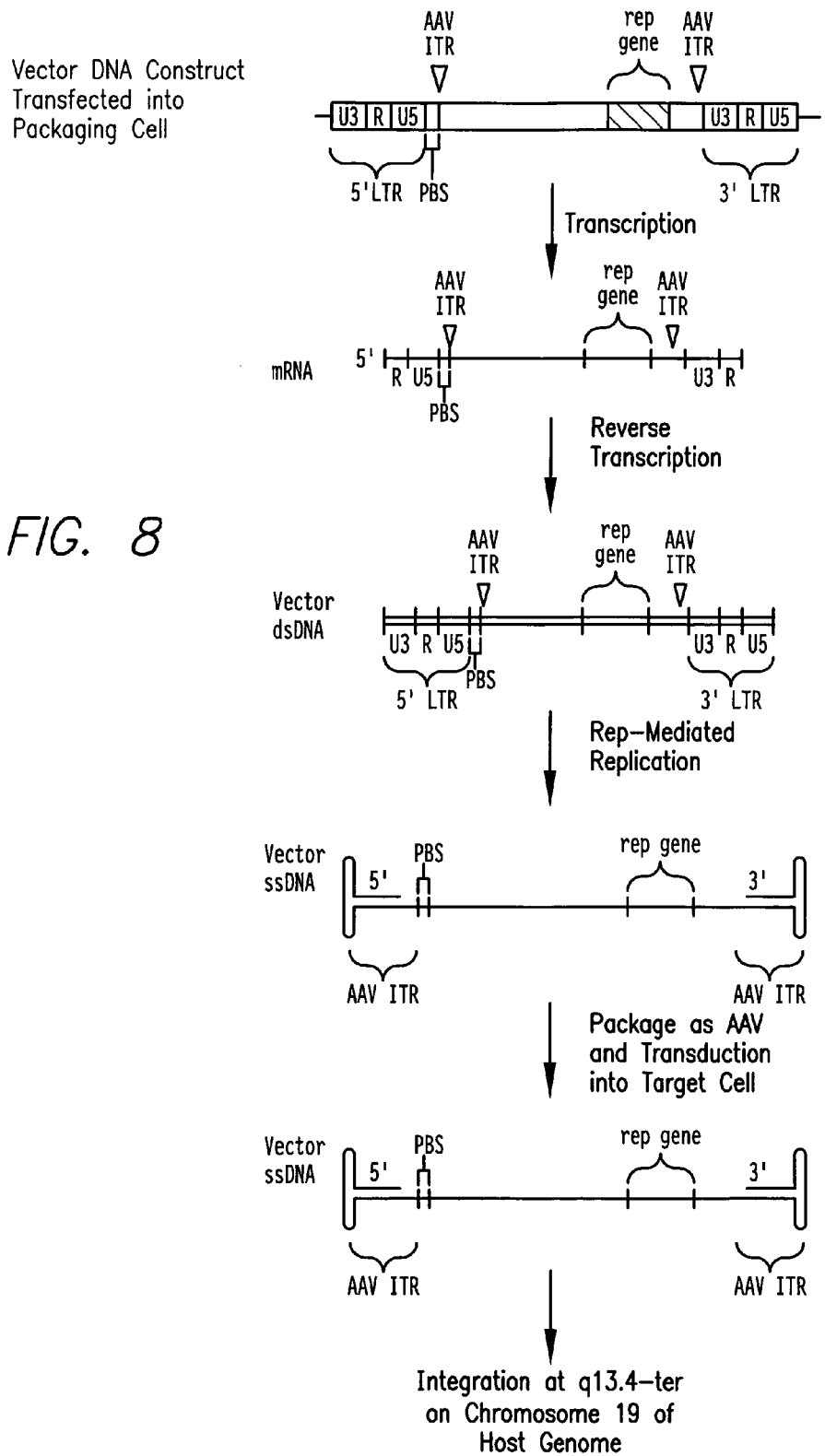
FIG. 8 illustrates the construction of a retroviral vector DNA construct that contains two adeno-associated virus (AAV) ITR sequences whereby one sequence is inserted into a site immediately downstream from the primer binding site and the other sequence is inserted into a site just upstream from the retrovirus origin for second strand synthesis (ppt).
Figure 9:
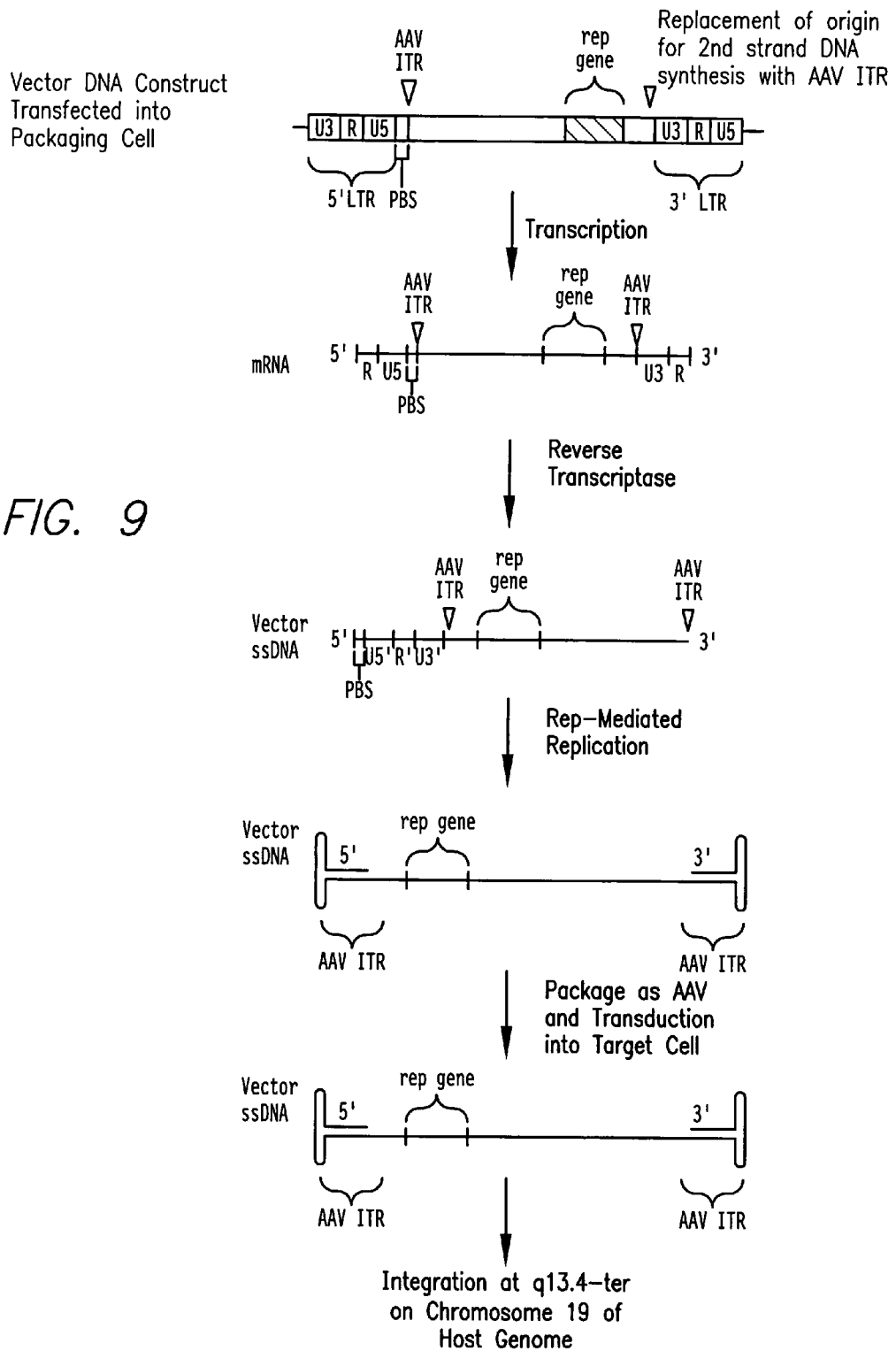
FIG. 9 illustrates the construction of a retroviral vector DNA construct containing two AAV ITR sequences whereby one sequence is inserted into a site immediately downstream from the primer binding site and the other sequence is inserted into a site from which the ppt sequences have been deleted.
Figure 10:
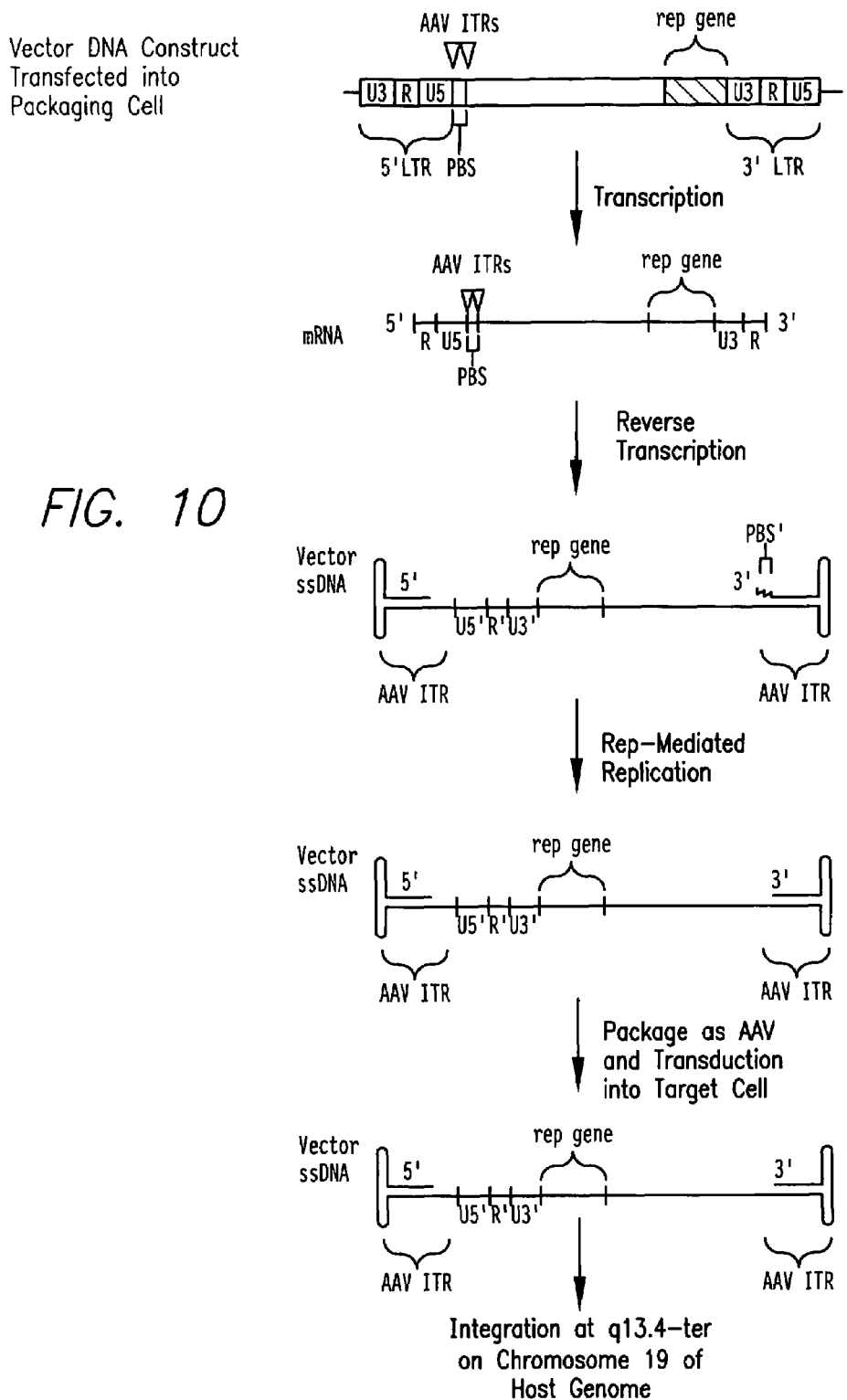
FIG. 10 illustrates the construction of a heterologous vector (retrovirus vector) DNA construct containing two AAV ITR sequences that flank the primer binding site (PBS).

An example of a virus vector that provides for production of an second vector by virus metamorphosis is presented in Examples 7, 8 and 9, and FIGS. 8, 9 and 10. AAV ITRs and sequences for AAV rep are inserted into an MMLV retrovirus vector sequence contained in a vector construct. A packaging cell is prepared from mouse 3T3 cells by the stable insertion into said cell of retrovirus reverse transcriptase sequences in order to provide for reverse transcription of retrovirus vector transcripts and sequences for AAV cap to provide for AAV virus vector packaging. Following introduction of the initiating retrovirus nucleic acid component (present on a plasmid) into a into such a packaging cell, reverse transcription of the retrovirus vector genome yields a single stranded retrovirus DNA containing two AAV ITR sequences that are separated by approximately 4.5 kb wherein they flank an AAV rep gene and a sequence for Exogenous Nucleic Acid. Such DNA copies, by virtue of the AAV ITR sequences and the AAV rep function can be replicated to produce AAV vector sequences which contain the AAV rep sequences and the Exogenous Nucleic Acid sequence. The presence of cap proteins and the AAV packaging signal provide for packaging of such AAV vector viruses.

This invention also provides a packaging cell line for propagating any of the viral vectors of the present invention, as disclosed or claimed herein. Such packaging cell line can provide, for example, at least two packaging components for the surface or envelope of the viral vector. In the packaging cell line, the cell line can be native to the viral vector. The viral vector itself can comprise in preferred aspects a retrovirus. The cell line for use in the packaging line of this invention, can take on a number of forms known in the art, including, for example, any of the members selected from the group consisting of NIH 3T3, U937, H9 and 293, or a combination of any of the foregoing.

In other aspects, any sequences for both the surface or envelope components in the packaging cell line are stably integrated in a chromosome or chromosomes of the packaging cell line. Furthermore, a sequence of a surface or envelope component can be stably integrated in a chromosome or chromosomes of the packaging cell line, and a sequence of another surface or envelope component can be transiently expressed. Still yet further, a sequence of said envelope component can be stably integrated in a chromosome or chromosomes of said packaging cell line, and a sequence of the surface component is transiently expressed. In other aspects, any sequence for both the surface or envelope components in the packaging cell line can be transiently expressed.

This invention also provides a packaging cell line for propagating other viral vectors as disclosed or claimed herein. In such instances, the cell line can be non-native to the viral vector component or components but native to the viral vector nucleic acid. The packaging cell line expresses on its membrane or its surface a receptor or receptors or binding partner or partners for adsorption to the non-native component for the vector.

Virus metamorphosis can also provide for integration of Exogenous Nucleic Acid into a cell genome. The ability of the second vector nucleic acid to integrate into the host genome provides distinct advantages for establishing stable expression of Exogenous Nucleic Acid in a target cell. However, some viruses lack this property but possess other useful properties for gene delivery, such as affinity for certain cell types, stability in human or animal tissues, efficient delivery of nucleic to target cells. The present invention provides compositions and methods of use for virus vectors that, through compositions for virus metamorphosis, can provide for the integration of Exogenous Nucleic Acid into a target cell genome. Such compositions can also provide for such integration to occur at preferred sites in the target cell genome.

Virus vectors possessing integration properties can be constructed by the incorporation of non-native components into the virus vector genome. Such useful components include such entities as certain nucleic acid sequences such as those containing integration signal sequences and certain vector nucleic acid conformations such as secondary structure. Non-native components useful for these purposes include such nucleic acid sequences such as retrovirus LTRs, reverse transcriptase and integrase that can provide for integration at random sites in a target cell genome. Virus vectors can also be modified with non-native components that provide for integration at preferred sites in a target cell. Such sequences include ITR sequences and the rep genes derived from AAV. These can be provided to a variety of virus vectors, including retrovirus.

Figure 11:
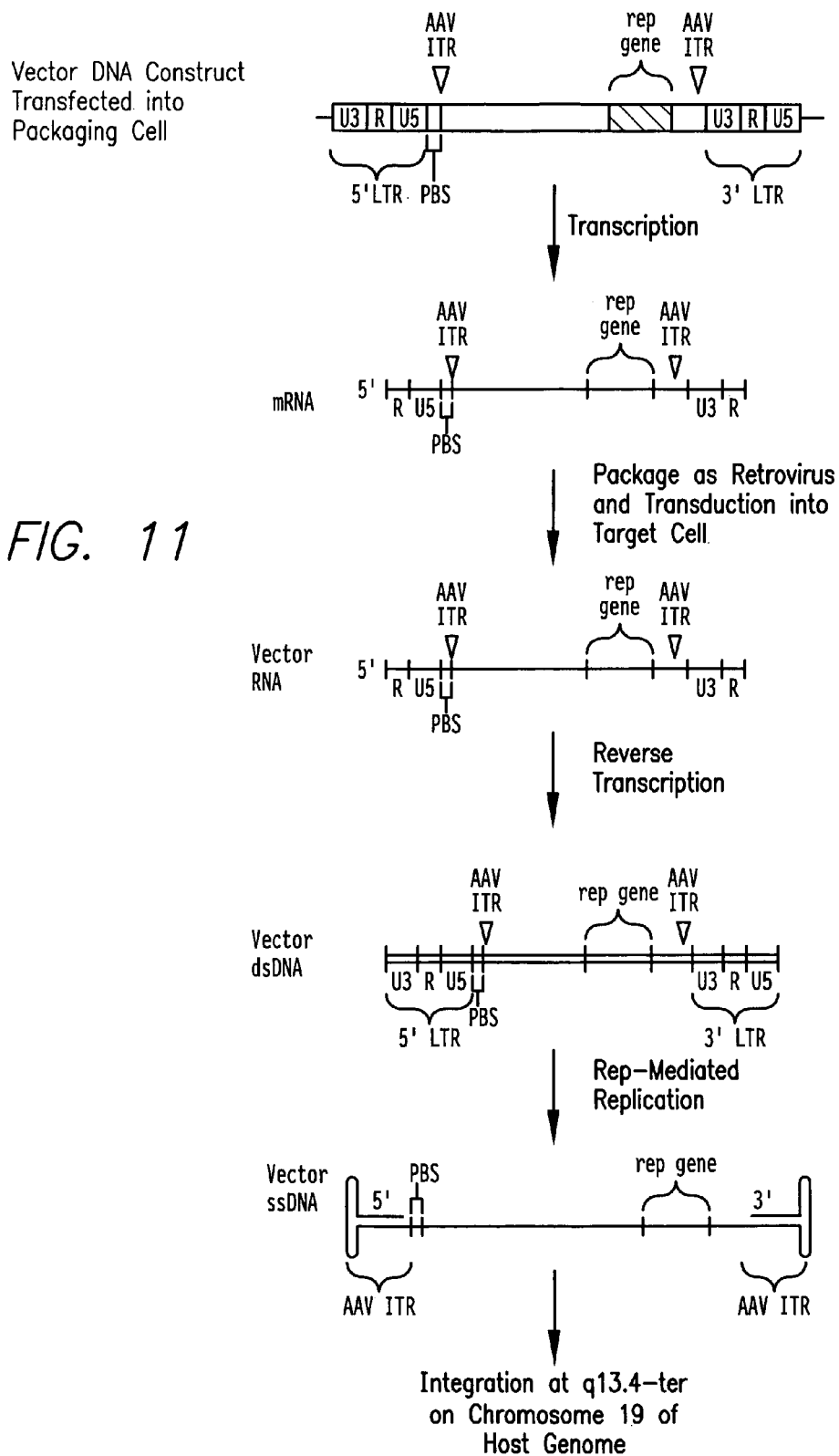
FIG. 11 illustrates the construction of a heterologous vector (retrovirus vector) containing two AAV ITR sequences whereby one sequence is inserted into a site immediately downstream from the primer binding site and the other sequence is inserted into a site just upstream from the retroviral origin for second strand DNA synthesis (ppt).
Figure 12:
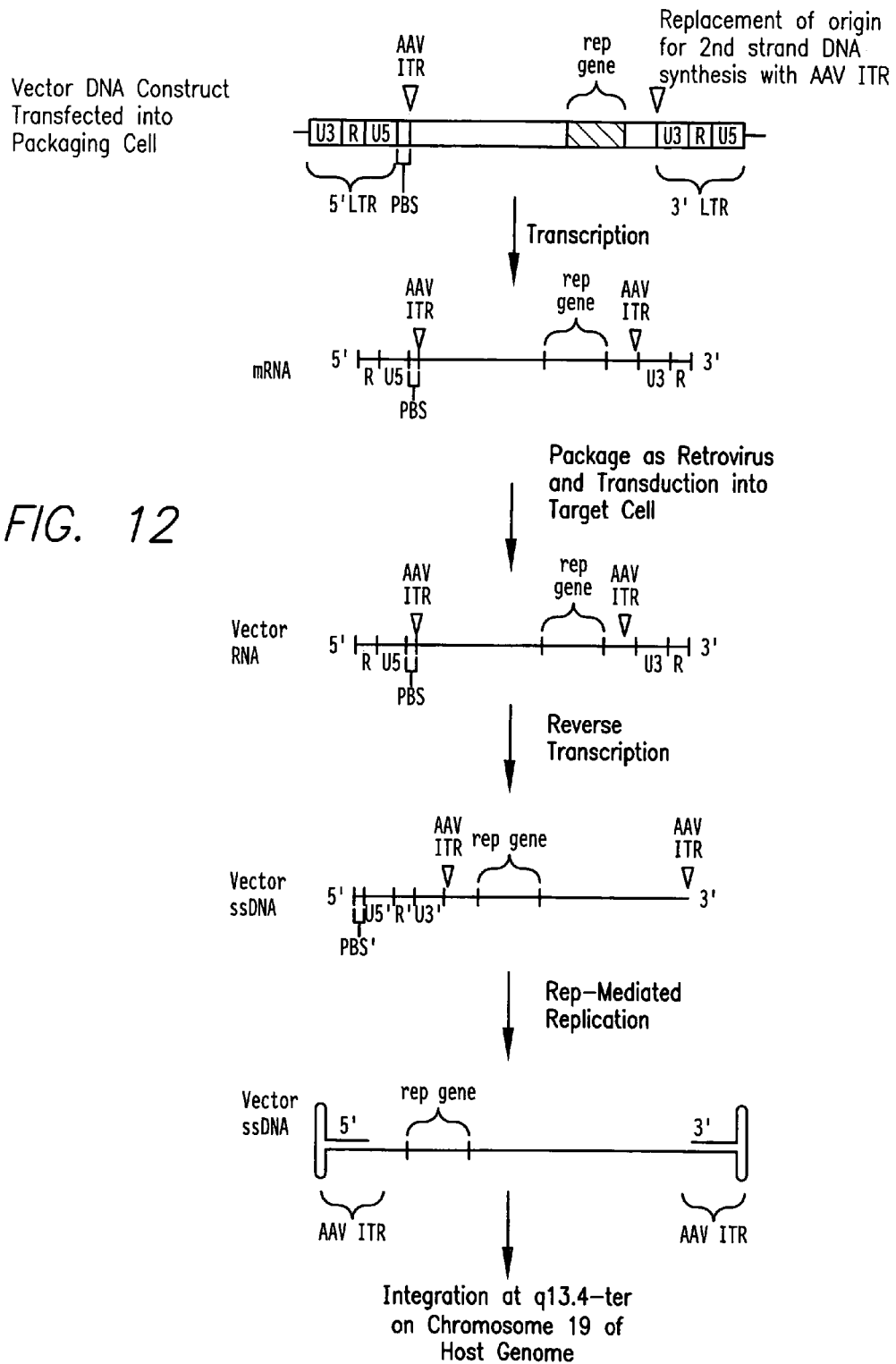
FIG. 12 illustrates the construction of a heterologous vector (retrovirus vector) containing two AAV ITR sequences whereby one sequence is inserted into a site immediately downstream from the primer binding site and the other sequence is used to replace the original retroviral sequences for second strand DNA synthesis (ppt).

Virus vectors containing non-native components that provide integration at preferred sites can be constructed by the methods of recombinant DNA as described above. Virus vectors such as retroviruses vectors can be modified for this purpose by the incorporation into the retrovirus nucleic acid component of two such ITR sequences wherein, following reverse transcription of vector RNA in a cell, the ITR sequences will flank a sequence or sequences containing Exogenous Nucleic Acid. Sequences for AAV rep function can also be incorporated into such a retrovirus vector genome or these sequences can be provided on a separate entity such as a virus or a nucleic acid construct such as a plasmid. The presence of the AAV ITR sequences in the double stranded product of reverse transcriptase and the AAV rep function in the cell can provide the capability for site specific integration into the target cell genome. This process is illustrated in FIGS. 10, 11 and 12. The process described above can also be performed through the production of a single stranded DNA product of the reverse transcriptase reaction. This can be achieved as described above by inactivation of the region of the retroviral genome involved in the initiation of second strand DNA synthesis, i.e., the ppt sequence (FIGS. 11 and 12).

Multitropic Virus Vectors

Gene delivery systems are known in the art. See, for example, Rabbani et al., U.S. patent application Ser. No. 08/574,443, filed on Dec. 15, 1995, contents of which are incorporated by reference herein.

For gene delivery purposes, a virus vector can be developed from a virus that is native to a target cell or from a virus that is non native to a target cell. In general it is desirable to use a non-native virus vector rather than a native virus vector. While native virus vectors may possess a natural affinity for target cells, such viruses pose a greater hazard since they possess a potential for propagation in target cells. In this regard animal virus vectors, wherein they are not naturally designed for propagation in human cells, can be useful for gene delivery to human cells. In order to obtain sufficient yields of such animal virus vectors for use in gene delivery, however, it is necessary to carry out such production in a native animal packaging cell. However, virus vectors produced in this way normally lack any components either as part of the envelope or as part of the capsid that can provide tropism for human cells. For example, current practices for the production of non-human virus vectors, such as ecotropic mouse retroviruses like MMLV, are produced in a mouse packaging cell line. Although producing a high titter, this vector lacked affinity for the target human cell. Alternatively, amphitropic vectors could be used but the titter could be much lower.

This invention overcomes this limitation in the prior art by providing compositions and methods of use for novel virus vectors and for their production wherein such vectors contain at least two surface components that can confer tropism both for target cells and for packaging cells. The presence in these virus vectors of at least two such components can provide independent capabilities for the efficient propagation of said vector viruses in packaging cells and for the efficient gene delivery to target cells. Affinity for the packaging cell provides for propagation to high yields by the ability of propagated vector viruses to re-infect packaging cells and undergo repeated cycles of propagation.

A variety of compounds that can present themselves on the surface of a virus can be used for the purposes of this invention, and these can be derived from virus envelope or capsid proteins or from proteins derived from other biological systems that have affinity for animal, plant or human cells and that can be incorporated into a virus vector surface. Such compounds useful for this purpose include protein molecules that consist of the natural amino sequence of such a protein or of a portion thereof. Such proteins or fragments can be modified in whole or in part. Proteins that can present themselves on the surface of a multitropic virus vector can be chimeric molecules formed between a protein native to the vector virus or a fragment thereof and a protein non-native to said virus or a fragment thereof.

The proteins of multitropic vector can be native or non-native to said virus vector. Useful native proteins include the retrovirus ecotropic and amphotropic, polytropic or xenotropic env proteins. Non-native proteins useful for gene delivery to human cells include all of the envelope proteins from human viruses, e.g., gp120 derived from HIV-1 or HIV-2 that can provide tropism for CD4+ cells, env proteins of HTLVI and HTLVII that can provide tropism for T cells, the envelop proteins of hepatitis B virus (HBV) that can provide tropism for liver cells. Envelope proteins from influenza such as HA that can provide tropism to human cells can also be useful. Envelope protein from EBV can also provide tropism for human B cells.

Multitropic vectors can be conveniently produced in packaging cells that provide for the synthesis of such components. These components will incorporate into the virus envelope in such a packaging cell. Nucleic acid sequences that provide for the synthesis of such compounds can reside on one or more plasmids and such plasmids can be introduced into packaging cells. Such a nucleic acid construct can be present in an episomal state or can be integrated into the genome of the packaging cell or can be in a combination of both episomal and integrated states. Packaging can be carried out by the methods and processes as disclosed herein.

Multitropic vectors can be prepared from such viruses as retroviruses wherein they contain in the virus envelope two or more compounds that are native to said virus such as the ecotropic env protein of MMLV and the amphotropic, polytropic or xenotropic env proteins of MMLV. Packaging of such a multitropic vector can be carried out by compositions described above. The presence of the ecotropic env protein in the virus envelope of the vectors can provide for efficient propagation of said virus vector in packaging cells derived from mouse cells, and the amphotropic, polytropic or xenotropic env protein can provide for delivery to human cells.

For example, a packaging cell that can produce multitropic retrovirus vectors containing both the ecotropic env protein and an amphotropic, polytropic or xenotropic env protein can be made from a mouse packaging cell such as 3T3 cells. Such a packaging cell could be constructed by the introduction into the cell of one or more plasmids containing the sequences encoding the packaging components, i.e., gag and pol, and the two envelope proteins. A cell line that highly expresses the packaging components can be selected and cloned. The subsequent introduction of provirus vector DNA plasmid into such a packaging cell line can initiate production of multitropic vectors.

Multitropic virus vectors can also be prepared wherein such viruses are retroviruses that contain in the virus envelope two or more compounds, at least one of which is native to said virus, such as the ecotropic env protein of MMLV, and at least one compound that is non-native to the virus vector but has affinity to the target cell. Such a non-native compound as that can be derived from another virus envelope and further provides affinity for the target cell. For example, a packaging cell that can produce multitropic retrovirus vectors containing both a native ecotropic env protein and a non-native protein such as the HIV-1 gp120 can be produced in a mouse packaging cell such as a modified 3T3 cell. Such a multitropic virus vector can be produced as described above using nucleic acid sequences for production of gp120 in place of nucleic acid sequences for the amphotropic, polytropic or xenotropic env protein. The presence of the ecotropic env protein in the virus envelope of the propagated multitropic vectors can provide for efficient propagation of said virus vector in packaging cells derived from mouse cells, and the gp120 protein can provide for delivery to CD4+ human cells. As described just above, the proteins of multitropic vector can be native or non-native to said virus vector. Useful native proteins include the retrovirus ecotropic and amphotropic, polytropic or xenotropic env proteins. Non-native proteins useful for gene delivery to human cells include all of the envelope proteins from human viruses, e.g., env proteins of HTLVI and HTLVII that can provide tropism for T cells, the envelop proteins of hepatitis B virus (HBV) that can provide tropism for liver cells. Envelope proteins from influenza such as HA that can provide tropism to human cells can also be useful. Envelope protein from EBV can also provide tropism for human B cells. All of the foregoing components could be propagated in a similar manner.

The present invention also provides compositions and methods of use for virus vectors that contain in the virus envelope or in the virus capsid at least one component that is non-native to said virus but is native to a target cell. Such a component could be a ligand for a target cell receptor. Efficient propagation of such a virus vector (herein designated as a monotropic virus vector) can be attained by the use of a packaging cell that is native to said virus and that has been modified to contain on its cell surface a receptor for the non-native viral component.

Monotropic virus vectors thus possess the same advantages as multitropic vectors for the efficient delivery to a target cell. These vectors exhibit the efficient adsorption similarly to a native virus to its target cell. These vectors lack, however, the undesirable risk to a human subject posed by a native virus. Thus, vector viruses such as animal retroviruses like MMLV can provide the advantages of a native virus vector without its dangers. Thus, for example, monotropic properties can provide for animal viruses to be utilized for gene transfer to human cells by the incorporation into the virus envelope or onto the virus surface of any of a wide variety of compounds non-native to said virus wherein such compounds provide tropism for certain types of cells. Efficient propagation of monotropic viruses that lack a native compound for affinity to native packaging cells can be attained by modifications made to such packaging cells. Thus, a cognate cellular receptor or receptors corresponding to the non-native component which is present on the virus surface or associated with the virus envelope can be introduced onto the surface of a packaging cell native to the virus vector. As an alternative approach, human cells for packaging of animal virus can be developed by providing all sequences for packaging components such as gag, pol and env from HIV (gp120).

A variety of compounds non-native to a virus vector that can present themselves on the surface of a virus or associate with the virus envelope can be used for the preparation of monotropic virus vectors, and these can be derived from envelope proteins or from proteins that provide affinity for animal, plant or human cells that can be derived from viruses or from other biological systems. Such compounds can include ligands derived from viruses, protein ligands derived from cells and proteins or peptides that can provide fusion with cell membranes. Such compounds useful for this purpose include protein molecules wherein such proteins can consist of the entire amino sequence of such a protein or of a portion thereof or wherein such proteins or fragments thereof or contain partially modified sequences.

Propagation of monotropic virus vectors can be conveniently performed in packaging cells that are native to the virus vector or native to a ligand present in a virus vector wherein such cells have been modified by the introduction of one or more non-native components that can act as receptors for monotropic viruses. Thus, an monotropic animal virus vector could, for example, contain a non-native ligand that provides for tropism to human cells. Propagation of said vector could be realized by propagation in a packaging cell native to the virus vector that has been modified to contain on its surface a receptor corresponding to the non-native ligand present on the monotropic virus. Such receptors can be introduced into packaging cells by the incorporation of nucleic acid sequences that provide for the synthesis of such receptors. Such nucleic acid sequences could be present in the cell either in an integrated (into the cell genome) or in an episomal state. The propagation of monotropic virus vectors can proceed by the introduction into the cell (native or non-native cell) of nucleic acid sequences for the virus vector nucleic acid and for the packaging components, including the non-native compound, wherein expression can proceed from these sequences present in an episomal state or in an integrated state A monotropic virus vector, such as, for example, a retrovirus vector such as MMLV, could be prepared to contain a non-native component (such as gp120) that provides tropism for specific types of human cells as well as for a modified mouse packaging cell. Such a vector will possess tropism for CD4+ human cells as well for modified packaging cell derived from mouse 3T3 cells that have been modified by the incorporation of nucleic acid sequences coding for CD4 and CCR-5 receptor proteins on the cell surface (Maddon, P. J., et al., Cell 47:33, 1986, incorporated by reference herein). Vector production could be carried out, for example, by a reverse packaging process as describe elsewhere in this patent by the stable incorporation into the genome of said cell of nucleic acid sequences that code for vector nucleic acid sequence. Propagation can be initiated by the introduction into such cells of nucleic acid sequences that provide synthesis of the packaging components of said retrovirus wherein such nucleic acid sequences include sequences for gp120 but not for a native env protein, i.e., neither the ecotropic or the amphotropic env proteins native to MMLV. Such sequences can be present on plasmids that can be amplified such as described elsewhere in this patent to provide for maximum synthesis of packaging components.

Packaging Systems

In general, the propagation of a viral vector (without a helper virus) proceeds in a packaging cell in which a nucleic acid sequence for packaging components were stably integrated into the cellular genome and nucleic acid coding for viral nucleic acid is introduced in such a cell line. In such a system, the packaging components availability is a limiting element for packaging, which leads to low titter or loss of continuous stability of nucleic acid sequence related to packaging components, and could lead to a packaging cell incapable of viral production.

To overcome these limitations, the present invention provides methods and compositions for novel reverse packaging systems that provide for efficient synthesis of packaging components without the use of helper virus and may further reduce or eliminate the probability for recombination events that can lead to the appearance of recombination competent virus by use of cDNA of a gene fragment or by any methods to minimize overlapping sequences of plasmids carrying sequences coding for packaging components.

Such a composition provided by this invention comprises a packaging cell wherein the nucleic acid sequence coding for the production of a virus vector nucleic acid components is stably integrated into the cell's genome. The packaging cell further provides all necessary packaging components. The use of such a reverse packaging system can overcome the limitations of other packaging systems by providing for optimal synthesis of packaging components, which can be accomplished by amplified expression of packaging components following transfection or by compositions and the methods described in full detail below.

Optimal expression of packaging components in the packaging cell where the sequence coding for vector nucleic acid is stably integrated into the cellular genome is achieved by introduction of a nucleic acid construct or constructs coding for packaging components. Such components could be native or non-native to the vector, or can be derived from genomic DNA or cDNA or any fragments thereof, or modification thereof. The nucleic acid construct coding for such packaging components could be present in packaging cell line in one or more copies.

Compositions for reverse packaging can provide optimal synthesis of virus vector packaging components by the use of nucleic acid amplification. Such amplification can be used in combination with highly efficient promoters for expression of packaging components as described above. Useful elements for the amplification of nucleic sequences for vector virus packaging components include the origin of replication for SV40 virus (SV40 ori) and the origin of replication for Epstein-Barr Virus (EBV ori). These elements can act to amplify a plasmid or other nucleic acid entity which contains sequences for the expression of vector components. Amplification of sequences by the use of plasmids or other nucleic acid entities whose replication is controlled by the SV40 ori can be accomplished by the expression in a packaging cell of trans-acting T-antigen, while amplification by the use of plasmids or other nucleic acid entities whose replication is controlled by EBV ori can be accomplished by the expression of EBNA. Cells with properties for the packaging of vector virus through amplification can be realized using EBV ori and EBNA.

For example, compositions for reverse packaging cells which utilize nucleic acid amplification can be prepared as described above for reverse packaging of virus vectors but wherein a packaging cell that efficiently and stably produces virus vector nucleic acid is transfected with one or more nucleic acid constructs containing SV40 ori or EBV ori wherein such nucleic acid constructs provide for the synthesis of packaging components. The trans acting T antigen or EBNA proteins can be produced from sequences present in the cell prior to transfection with said nucleic acid constructs or they can be present on said nucleic acid constructs.

Compositions and methods of use for reverse packaging systems can provide for greatly reducing or eliminating the possibility of recombination events among nucleic acid segments that encode virus vector nucleic acids and packaging components wherein such recombination events could give rise to replication competent viruses. This can be accomplished by elimination of overlapping regions of virus genome between two such segments in packaging cells.

An example of a packaging system that markedly reduces or eliminates such possibility for recombination events and which can be used in combination with reverse packaging and/or amplification compositions as described above for the propagation of retrovirus vectors can be made by cloning of the retrovirus sequences for gag, pol and env wherein the sequences for LTR are not included. The gag, pol and env sequences can be prepared from cDNA preparations and cloned into a nucleic acid construct such as a plasmid. All such sequences can be cloned into the same plasmid wherein they can be expressed from one or more promoters, or such sequences can be cloned into two or more plasmids wherein two or more such plasmids are required to provide all of the required sequences for viral packaging components and wherein at least one promoter is required for expression in each plasmid.

A variety of non-native promoter/enhancer elements, along with polyadenylation signal, can be used for driving cDNA expression. Promoters/enhancers which are highly efficient and either constitutive or inducible can be used. These include but are not limited to promoters derived from cellular genes, such as the metallothionen promoter/enhancer and the elongation factor (EF) promoter/enhancer, or promoters derived from viruses such as CMV early promoters/enhancers, including the promoter/enhancer for the CMV E1 a gene, promoters derived from bacteriophages such as T3, T7 and SP6 when expression of cognate polymerases can be established in a packaging cell. The use of promoters/enhancers such as the metallothionen promoter/enhancer can provide for the induction of expression of vector components in packaging cells.

Cells suitable for packaging retroviruses can be transfected with a plasmid that contains sequences for the expression of vector nucleic acid and a stably transfected cell line producing vector nucleic acid can be selected. Retrovirus vectors can be produced by transfection of this cell line with one or more nucleic acid constructs, such as plasmids, that provide for expression of packaging components. The propagation of retrovirus vectors can proceed from a transient transfection or from a stable transfection with plasmids that provide for packaging components.

Non-Viral Specific Nucleic Acid Complexes (NVS Complexes)

The present invention provides compositions and methods of use for non-viral specific nucleic acid complexes (NVS complexes) that can offer significant advantages for the use of non-viral vectors in gene delivery. Such NVS complexes are composed of a nucleic acid component and one or more specific binding proteins that bind to one or more specific nucleic acid sequences in the nucleic acid construct. Previous compositions for non-viral nucleic acid complexes for gene delivery have relied on non-specific complexes between nucleic acid component and polypeptides or polycationic polymers lipids. A wide variety of such entities have been used wherein binding to the nucleic acid sequences is non-specific and/or ionic. It is recognized, however, that such non-specific binding to nucleic acid can interfere with function of such nucleic acid, such as transcription, integration, transport into the cell and/or into the nucleus and can have other interfering effects including toxicity.

While non-viral nucleic acid complexes can provide significant advantages for gene delivery, these advantages have not or cannot be realized by the use of non-specific nucleic acid complexes that rely on non-sequence specific binding components. The present invention overcomes these limitations by providing for specific complex formation between specific nucleic acid sequence and protein components wherein the binding of protein molecules that provide useful properties for gene transfer can be localized to defined regions of the nucleic acid construct. Such localization of specific binding proteins in the nucleic acid construct can reduce or eliminate any interference with regions of the nucleic acid component that provide biological activity. The present invention also provides for the controlled displacement of such specific binding proteins from their cognate binding sites wherein such displacement can remove any possible interference with biological function or can release proteins that can provide useful function in the cell.

The present invention provides compositions and methods of use for non-viral specific nucleic acid complexes (NVS Complexes) that, upon introduction into a cell, are capable of biological function, i.e., gene expression, transcription, translation, integration, intracellular transport, production of a protein in a cell, production of a nucleic acid in a cell or interaction with a nucleic acid or protein in a cell. The present invention can provide significant advantages for non-viral vectors through the use of specific binding proteins that attach to cognate nucleic acid sequences in the vector nucleic acid component and can render the construct capable of one or more of the following properties: 1) binding to a target cell, 2) providing for introduction of the nucleic acid component into cells, 3) providing for localization to sites within a cell, 4) providing a signal for integration into cellular DNA, 5) providing enzymatic activity for replication and/or expression of vector nucleic acid within the cell 6) providing protection of the nucleic acid component from degradation both in vivo and in vitro. In the present invention one or more of the above properties can be provided without substantially interfering with biological function of said vector nucleic acid.

The present invention provides advantages over non-viral complexes that rely on non-specific or ionic binding between nucleic acid and polypeptides or lipids by the use of specific binding proteins that can recognize specific nucleic acid sequences in the vector nucleic acid component and thus provide the capability to segregate regions of specific protein binding from sequences in the nucleic acid component that provide biological function. Thus, one or more of the above properties can be provided without substantially interfering with biological function of the nucleic acid component. Such specific sequences are not an element or a part thereof of a gene expression cassette such as a promoter sequence, but if promoter sequences are used then they are not involved in transcription but only function to bind peptides. Transcription from such sequences can be limited or eliminated by the use of inverted nucleic segments or inverted nucleotides immediately downstream from such promoter sequences.

The specific binding proteins of NVS complexes can further attach through fusion, conjugation, or complexing either directly or indirectly to other moieties including natural or unnatural, modified or unmodified oligo- or polypeptides; polycations; natural or unnatural, modified or unmodified oligo- or polysaccharides; multimolecular complexes; inactivated viruses; lipids; and ligands. Such components can have enzymatic activity such as polymerase activity or protein with any biological function including transport and integration. The NVS complexes of the present invention can provide for the delivery of nucleic acid to eukaryotic cells including the cells of plants, humans and other mammals and to prokaryotic cells.

Specific binding protein molecules and their cognate nucleic acid sequences useful to the practice of this invention include: the bacteriophage λ repressor

TATCACCGC

ATAGTGGCG;

the bacteriophage 434 repressor

AC AAGAAAA

T GTTC T TT T;

the tryptophan repressor of E. coli

GTACTAGTT A

CATGATCAAT;

the Met J repressor of E. coli,

AGACGTCT

TCTGCAGA;

the lac repressor of E. coli,

T G G A AT T G T G A G C G G A T A A C A A T T

ACCTTAACACTCGC CTATT GTTAA; (SEQ ID NO:5)

the Engrailed gene regulator protein of Drosophila,

TAAT

ATTA;

the MATα2 yeast repressor protein,

CATGTAATT

GTACATTAA;

the CAP gene activator of E. coli

AAAAGTGTG ACAT

TTT T CACACTGTA; (SEQ ID NO:8)

the GAL4 yeast transcription activator,

CCGGAGGACAG

GGCCTCCT GTC;

the E2 papillomavirus transcription regulator,

ACCGACGTCGGT

TGGCTGCAGCCA;

the yeast GCN4 transcription regulator,

ATGATC

TACTAG;

the zif268 murine gene regulator,

GCGTGGGCG

CGCACCCGC;

the glucocorticoid receptor transcription modulator,

CAGAACATC

GTCTT GTAG;

the TFIID transcription initiation factor,

TATATAAA

ATATATTT.

Cognate sequences can be part of a nucleic acid construct and can be present at one or more sites in the nucleic acid construct wherein one or more such sequences can be present at any one site. Thus the number of such cognate nucleic acid sequences can be so arranged in order to achieve one or more objectives including nuclease resistance. Furthermore, the presence of multiple copies of such sequences in a repeated array can provide for a desired binding constant between the nucleic acid and a binding protein. Two or more such sequences can be present in a nucleic acid component to provide for association with two or more different kinds of specific binding proteins.

Useful properties can be provided to NVS complexes by protein/nucleic acid interactions that can be dissociated in a controlled manner. Thus, for example, as a means of eliminating any interference of bound proteins with biological function of the nucleic acid component, a dissociable specific binding protein can be bound to its cognate sequence in the nucleic acid component and, following contact of the NVS complex with the target cell but prior to expression of biological function, said complex in the cell can be exposed to a molecule that induces dissociation. Such proteins as the lac repressor of E. coli and its cognate sequence are useful in this regard wherein dissociation can be effected by an inducer such as an appropriate saccharide or IPTG. It is preferred that when such a complex carrying another component that needs to bind to nucleic acid to provide further function, e.g., such proteins as RNA polymerase or reverse transcriptase wherein such induced release will further improve such function provided by the NVS vector.

Specific binding proteins can be modified by chemical modification or by attachment to a variety of ligands that can provide useful properties for nucleic acid transfer to target cells. Such ligands or chemical modifications, being any chemical moiety, natural or synthetic, that can be utilized in this invention include macromolecules greater than 20,000 m.w. as well as small molecules less that 20,000 m.w. The ligand can include both macromolecules and small molecules. Macromolecules that can be utilized include a variety of natural and synthetic polymers including peptides and proteins, nucleic acids, polysaccharides, lipids, synthetic polymers including polycations, polyanions and mixed polymers. Small molecules include oligopeptides, oligonucleotides, monosaccharides, oligosaccharides and synthetic polymers including polyanions, polycations, lipids and mixed polymers. Small molecules can also include mononucleotides, oligonucleotides, oligopeptides, oligosaccharides, monosaccharides, lipids, sugars and other natural and synthetic entities.

Ligands and chemical modifications can be utilized to provide for nucleic acid transfer to cells by providing such useful properties as 1) binding to a target cell, 2) providing for introduction of the nucleic acid component into cells, 3) providing for localization to sites within the cell 4) providing a signal for integration into cellular DNA, 5) providing enzymatic activity for replication and/or expression of vector nucleic acid within the cell by such proteins as DNA polymerase, RNA polymerase, reverse transcriptase, DNA ligase. 6) Proteins that protect the nucleic acid component from degradation.

1) Cell targeting entities that can be utilized include:
  a) antibodies to cellular surface components and epitopes
  b) viruses, virus components of fragments of virus components that have affinity for cellular surface components. These include such proteins as the gp120 protein of HIV-1 or HIV-2 that binds to the CD4+ receptor of T4 lymphocytes (Lever 1995 British Medical Bulletin 51:149, the contents of which are incorporated by reference).
  c) ligands that have affinity for cell surfaces. These include hormones, lectins, peptides and proteins, oligosaccharides and polysaccharides. Two such ligands that could be used, for example, are asialoorosomucoid that binds to the cellular asialoglycoprotein receptor (Wu et al 1989 J Biol Chem 269:16985, the contents of which are incorporated by reference) and transferrin that binds to transferrin cellular receptors (Wagner et al. 1992 89:6099, also incorporated by reference),
  d) polycations such as polylysine that bind non-specifically to cell surfaces (Wu and Wu, U.S. Pat. No. 5,166,320 (contents fully incorporated by reference) wherein the function of a specific binding protein could be improved if the charge on the nucleic acid is neutralized.
  e) matrix proteins such as fibronectin that bind to hematopoetic cells and other cells (Ruoslahti et al. 1981 J Biol Chem 2:7277, the contents of which are incorporated by reference).
2) Entities that facilitate cellular uptake include inactivated viruses such as adenovirus (Crisitiano et al. 1993 Proc Natl. Acad. Sci. USA 90:2122) Curiel et al. 1991 Proc Natl Acad. Sci. USA 88:8850): virus components such as the hemaglutinating protein of influenza virus and a peptide fragment derived from it, the hemagglutinin HA-2 N-terminal fusogenic peptide (Wagner et al. 1992 Proc Natl. Acad. Sci. USA 89:7934). The contents of each of the foregoing publications are incorporated by reference.
3) Entities that confer cellular location include:
  a) nuclear proteins such as histones
  b) nucleic acid species such as the snRNAs U1 and U2 (which can be conjugated to binding proteins in accordance with known method, see, for example, Pergolizzi et al., U.S. patent application Ser. No. 06/491,929, filed on May 5, 1983, now abandoned the contents of which are incorporated herein by reference) which associate with cytoplasmic proteins and localize in the nucleus (Zieve and Sautereauj, 1990, Biochemistry and Molecular Biology 25: 1, the contents of which are incorporated by reference).

4) entities which facilitate incorporation into cellular nucleic acid include:

a) proteins that function in integration of nucleic acid into DNA. These include integrase site specific recombinases (Argos et al. 1986 EMBO Journ 5:433, incorporated by reference) and 5) Entities such as nucleic acid polymerases that act to replicate vector nucleic acid sequences. These include such enzymes as reverse transcriptase, RNA polymerases such as derived form *E. coli*, T7 bacteriophages, and other virus, prokaryotic and eucaryotic systems.

6) Entities such as that provide protection of the nucleic acid component from degradation both in vivo and in vitro. Chemical modifications or ligands can be fused, attached or conjugated directly or indirectly to specific binding proteins by covalent or non-covalent methods to provide such properties as described above. Thus a specific binding protein or a fragment thereof can be fused to a protein, such as a ligand, or a fragment thereof, wherein the fused protein is a chimeric molecule with properties provided by both proteins. Such a fused molecule can be prepared by the methods of recombinant DNA or by chemical synthesis. Such fused proteins can also be prepared wherein three or more proteins, or fragments thereof, can be fused to form a chimeric protein molecule. Such proteins may contain useful properties provided by each of the constituent protein entities, or one or more such sequences can act as a connector between polypeptide sequences that provide function. Covalent linkage of protein ligands to specific binding proteins by direct linkages can be by methods practiced in the art including direct or indirect chemical attachment to reactive sites in a specific binding protein. Such covalent attachment could also be indirect wherein a specific binding protein can be attached to a protein that is, in turn, modified by attachment to a compound or protein that provides useful function. Non-covalent methods that can be utilized include modification of the specific binding protein to provide for direct or indirect and/or specific or non-specific binding of useful molecules including antigen-antibody interactions, receptor-ligand interaction, by hydrophobic interaction, polyionic interaction. Thus a specific binding protein could contain native properties for binding to an antibody, or could be attached to contain a compound that can be bound by an antibody. Such an antibody could, in turn, be modified by attachment to a protein or other compound that provides useful function. Specific binding proteins could also be modified to contain ligands such as biotin that can provide binding to proteins such as avidin or streptavidin. Other useful ligands that can be used include lectins.

The nucleic acid component of an NVS complex can be DNA, RNA, a combination of RNA and DNA, e.g., a DNA-RNA hybrid or a chimeric nucleic acid such as a DNA-RNA chimera. The nucleic acid components of a NVS complex can be single stranded, double stranded or triple stranded. The nucleic acid component be circular, linear or branched and may take the form of any DNA or RNA, and it can contain both double stranded regions and single regions. All or part of the nucleic acid component can be composed of modified nucleic acid or nucleic acid analogues. All or part of the nucleic acid component can be prepared by chemical or enzymatic methods.

Nucleic acid sequences recognized by specific binding proteins can be present in the nucleic acid component in one or more copies. More than one kind of such a cognate sequence can be present in a nucleic acid component in order to provide for binding of two or more different kinds of specific binding proteins. Multiple copies of cognate sequences can be present in close proximity one to another such as in one or more tandem array or such sequences can be present at sites throughout the nucleic acid component.

Regions of biological activity in the nucleic acid component of NSV complexes can specify coding for RNA (such as antisense RNA or ribozymes) or for RNA that can be translated into protein. Regions of biological activity in NVS complexes can contain sequences for hybridization with intracellular nucleic acid sequences, integration into cellular DNA, termination sequences, primer sites and promoter sites.

A NVS complex can be prepared, for example, using a nucleic acid component such as a plasmid that contains nucleic acid sequences that can provide biological function cell and cognate nucleic acid sequences recognized by a specific binding protein such as the lac inducer region (Lac i) that can provide for the binding of lac repressor protein. Sequences for the lac inducer region can be included in multiple copies in order to provide for binding of multiple copies of lac repressor protein. In order to avoid any interference of biological activity by the lac repressor, the multiple copies of the lac inducer sequence can be localized to a region of the plasmid that is separate from sequences providing biological function. The lac repressor protein for these purposes can be modified to provide to provide useful properties for gene transfer. Thus, the lac repressor could be modified to provide for binding to a target cell by conjugating, fusing or complexing with a protein that provides affinity for targeted cells. Thus, such proteins as the gp120 protein derived from HIV-1 that has properties for attachment to CD4+ cells or the surface antigen of HBV that provides affinity for liver cells could be used. Sattentau, Q. J. and Weiss, R. A., Cell 52:631-633 (1988); Robinson, W. S: Hepandnavividae and their replication in Field, B N (ed.), *Virology, Vol. 2*, Second ed., 1989; pages 2137-2169, incorporated herein by reference.

An NVS complex can also contain more than one kind of specific binding protein in order to provide additional functions. A NVS complex could be constructed as described above wherein, in addition to the localized multiple copies of cognate sequences for lac repressor binding, additional regions of the nucleic acid component containing multiple copies of other specific binding proteins such as, for example, the bacteriophage 434 repressor and the bacteriophage λ repressor. These sequences can be also included in the nucleic acid component wherein they are present at sites separate from nucleic acid sequences providing biological function. The 434 repressor can be modified by conjugation, fusion or complexing to a nuclear localizing entity such as U1 RNA and the λ repressor can be modified by conjugation to an integrase in order to assist integration into the cell genome. Oraigie, R. et al., Cell 62:829-837 (19901, contents of which are incorporated herein by reference.

DESCRIPTION OF THE PREFERRED EMBODIMENTS

Example 1

Reconstitution of a Cis Effect that Resulted from the Inactivation of the U3 Promoter/Enhancer in a Heterologous Vector (Retrovirus Vector) by the Use of Irrelevant Sequence Replacement A Heterologous Vector (retrovirus vector) was prepared in which the LTR promoter and enhancer were inactivated wherein polyadenylation function was reconstituted. Replacements were made to a retroviral vector sequence (FIG. 1) present in a plasmid (pENZ1). A 188 base pair DNA fragment in the 3' LTR U3 enhancer was replaced by 188 base pairs derived from the bacterial Neo gene (neomycin phosphotransferase) sequence through PCR strategy. Two regions of the promoter, one of 2 base pairs and one of 6 base pairs, were each replaced by restriction enzyme recognition sequences of the same size through oligonucleotide-mediated site directed mutagenesis. The removed native sequences and the non-native replacement sequences are shown in FIG. 2.

The replacements of the enhancer and promoter regions were confirmed by DNA sequencing of these regions following manufacture's instruction (USB and ABI).

A complete Neo sequence was incorporated into this Heterologous Vector sequence. Heterologous Vector (retroviruses vector) were produced by transfection of a packaging cell line (PA 317 and GP+E-86) with the vector DNA construct. The propagated Heterologous Vectors (retrovirus vectors) were assayed in a transducing titer measuring Neo transductants of 3T3 cells. A titer of up to $10^6$ transducing particles per ml was obtained.

Example 2

A Retroviral Vector with Inactivated Promoter/Enhancer which Contains a Non-Native Polyadenylation Signal (the Mouse Histone H2A614 Gene)

Figure 3:
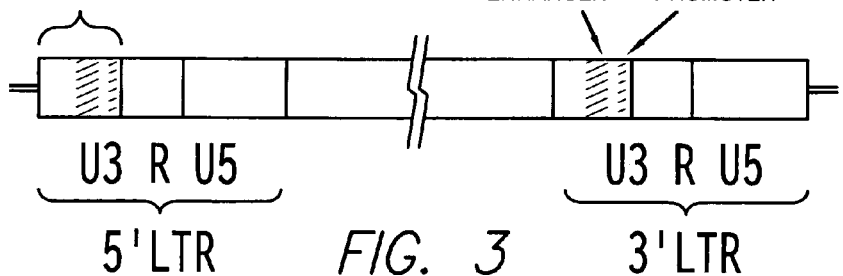
FIG. 3 depicts the general replacement strategy for a retroviral vector having an inactivated promoter/enhancer and a non-native polyadenylation signal (the mouse histone H2A614 gene).

The nucleic acid sequence of Heterologous Vector retrovirus present in a plasmid that contains a Neo gene in a region outside of the retrovirus vector nucleic acid sequence can be modified by (FIG. 3) by replacement of a 188 base pair region of the 3' enhancer with 188 base pairs derived from the bacterial Neo gene as described in Example 1. By the same methods, the promoter sequence can be replaced with sequences for a stem loop processing signal derived from mouse histone H2A614 gene. Retrovirus vectors containing these modifications can be produced by transfection of packaging cells with this plasmid vector and selection of a producer cell line. Such retrovirus vectors can be used for delivery of an Exogenous Nucleic Acid to a target cell wherein mRNA expressed from Exogenous Nucleic Acid can be polyadenylated by using the downstream element of both the non-native mouse histone H2kA614 stem-loop processing signal and the retrovirus AATAA element.

Example 3

A Retroviral Vector with Inactivated Promoter/Enhancer which Contains a Non-Native Polyadenylation Signal (the Human G-CSF Gene with the AATAAA and mRNA Destabilization Elements Removed)

Figure 4:
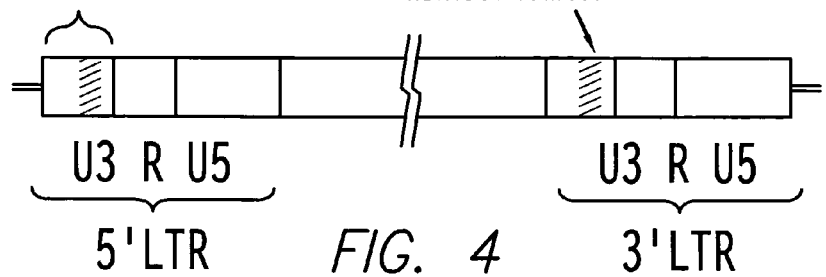
FIG. 4 depicts the general replacement strategy for a heterologous retroviral vector in which a polyadenylation processing signal from a human gene (G-CSF) with the AATAAA and mRNA destabilization elements removed is used to replace a region of the 3' U3 snRNA.

A Heterologous Vector (retrovirus vector) can be constructed in which the 3' LTR promoter and enhancer were inactivated wherein the endogenous retroviral polyadenylation site is used. Modifications to provide inactivation are made to a retroviral vector nucleic acid sequence present in a plasmid (pENZ-1). The region of the LTR containing the promoter/enhancer and the endogenous retroviral polyadenylation signal upstream from the AATAAA element was replaced with a portion of an efficient exogenous polyadenylation signal. In this way, vector mRNA can be polyadenylated by using the retroviral downstream AATAAA element. Here, a polyadenylation processing signal from the human G-CSF gene with the AATAAA and mRNA destabilization elements removed can be used to replace a region of the 3' U3 that encompasses both the promoter and enhancer sequences (FIG. 4). In the case, the retroviral AATAAA element is used.

Example 4

Transcription of Chimeric RNA from a Heterologous Vector Retrovirus Using a Promoter/Enhancer Recognized by Pol 1

Figure 5:
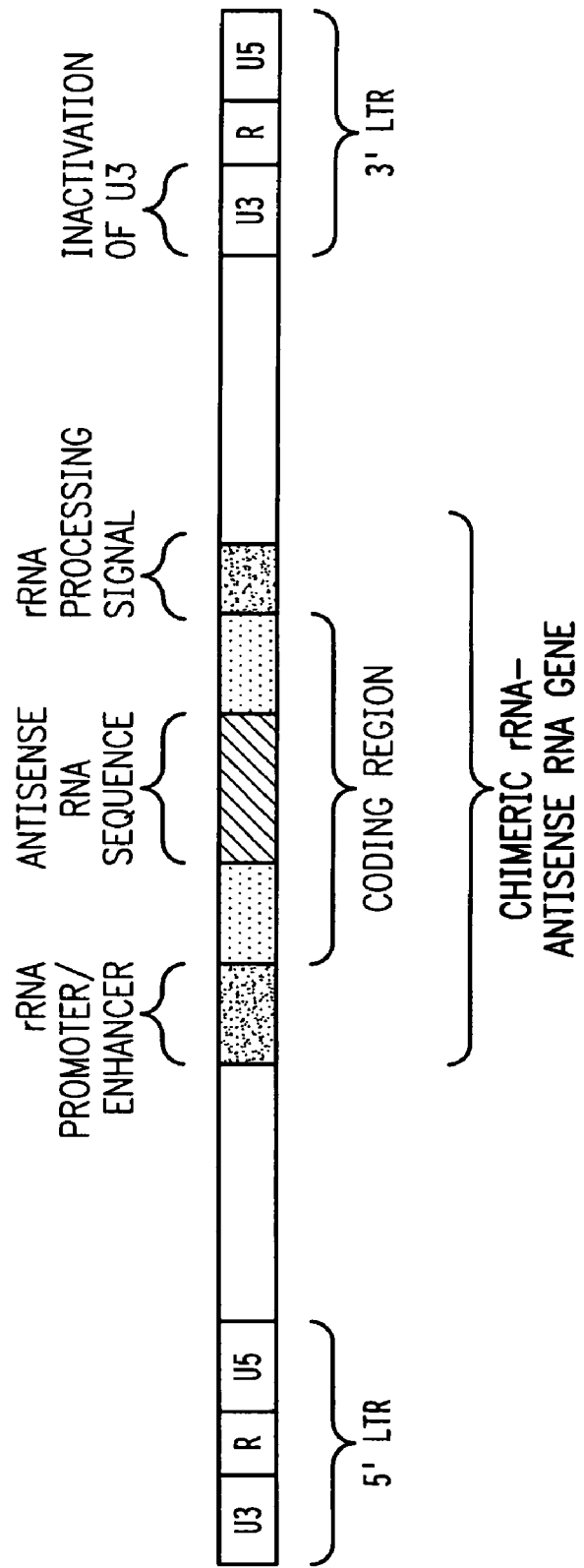
FIG. 5 depicts the general replacement strategy for constructing a heterologous retroviral vector for delivering an exogenous nucleic acid that transcribes a chimeric molecule composed of antisense RNA and rRNA.

A Heterologous Vector retrovirus can be constructed as described in Example 1 to deliver an Exogenous Nucleic Acid sequence that transcribes a chimeric molecule composed of an antisense RNA and rRNA (FIG. 5). A sequence such as Neo can be present residing outside of the Heterologous Vector sequence in the plasmid to provide for selection of producer cells. This vector construct is used to transfect packaging cells to produce Heterologous Vector retroviruses. The Heterologous Vector retroviruses are used to transduce a target cell. The polymerase I of the target cell provides for synthesis of the chimeric RNA from integrated Heterologous Vector DNA.

Example 5

Figure 6:
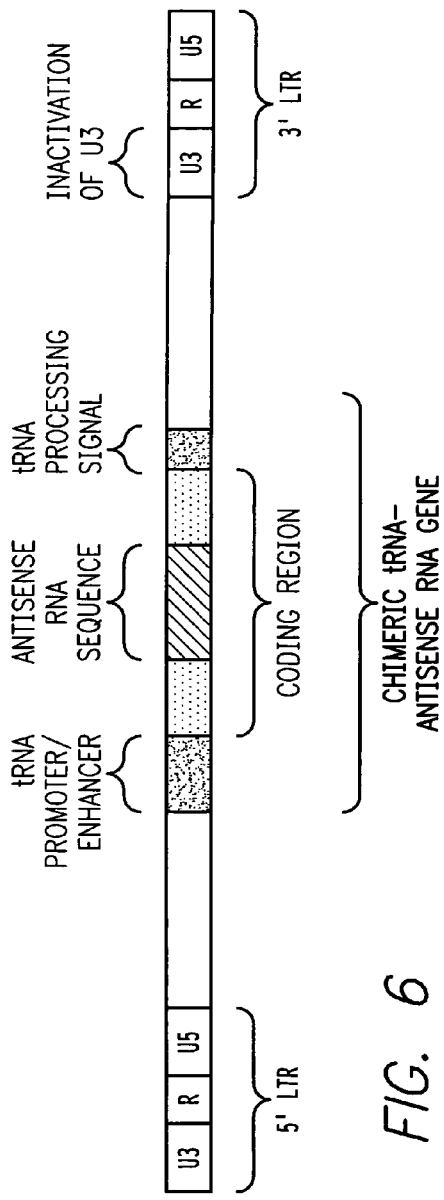
FIG. 6 also depicts the general replacement strategy for constructing a heterologous retroviral vector for delivering an exogenous nucleic acid that transcribes a chimeric molecule composed of antisense RNA and rRNA.

Transcription of Chimeric RNA from a Heterologous Vector Retrovirus Using a Promoter/Enhancer Recognized by Pol III A Heterologous Vector retrovirus can be constructed as described in Example 1 to deliver an Exogenous Nucleic Acid sequence that transcribes a chimeric molecule composed of an antisense RNA and tRNA (FIG. 6). A sequence such as Neo can be present in a region outside of the Heterologous Vector sequence in the plasmid to provide for selection of producer cells. This vector construct is used to transfect packaging cells to produce Heterologous Vector retroviruses. The Heterologous Vector retroviruses are used to transduce a target cell. The polymerase III of the target cell provides for synthesis of the chimeric RNA from integrated Heterologous Vector DNA.

Example 6

Figure 7:
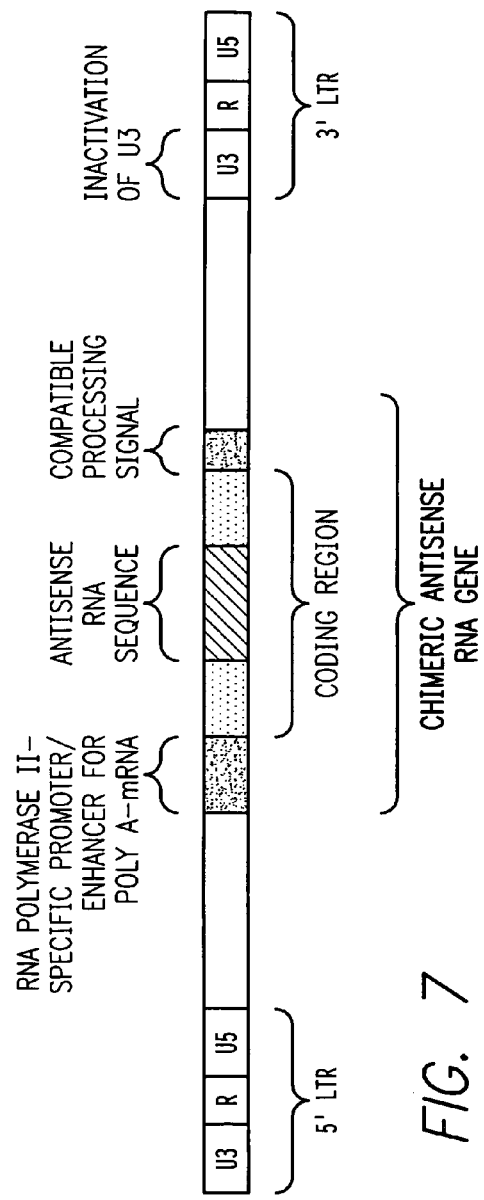
FIG. 7 also depicts the general replacement strategy for constructing a heterologous retroviral vector for delivering an exogenous nucleic acid that transcribes a chimeric molecule composed of antisense RNA and rRNA.

Transcription of Chimeric RNA from a Heterologous Vector Retrovirus Using a Promoter/Enhancer Recognized by Pol 11 Wherein the Transcript is not Polyadenylated A Heterologous Vector retrovirus can be constructed as described in Example 1 to deliver an Exogenous Nucleic Acid sequence that transcribes a chimeric molecule composed of an antisense RNA and the snRNA molecule U1 (FIG. 7). A sequence such as Neo can reside in a region outside of the Heterologous Vector sequence in a plasmid to provide for selection of producer cells. This vector construct is used to transfect packaging cells to produce Heterologous Vector retroviruses. The Heterologous Vector retroviruses are used to transduce a target cell. The polymerase II of the target cell provides for synthesis of the chimeric RNA from integrated Heterologous Vector DNA.

Example 7

Propagation of AAV Vector Viruses from a Heterologous Vector Retrovirus Containing Non-Native Vector Components Derived from AAV A retroviral vector DNA construct can be constructed to contain two AAV ITR sequences wherein one is inserted into a site immediately downstream from the primer binding site and the other is inserted into a site just upstream from the retrovirus origin for second strand DNA synthesis (ppt) such that following reverse transcription in a cell the ITR sequences will be separated by approximately 4.5 kb (FIG. 8). An Exogenous Nucleic Acid can be inserted between the AAV ITR sequences.

The sequences for the AAV cap protein and for the retrovirus for reverse transcriptase function are inserted into a plasmid such as pBR322. The sequences are expressed under the control of the promoter/enhancer of a constitutive cellular gene such as the elongation factor (EF).

The retroviral vector DNA construct and the plasmid containing the cap and the reverse transcriptase sequences are used to transfect a packaging cell. Transcripts of Heterologous Vector RNA are reverse transcribed to yield double stranded retrovirus vector DNA. The rep product can mediate synthesis of single stranded vector DNA wherein the rep sequences and the Exogenous Nucleic Acid are flanked by the AAV ITR sequences. The presence of cap protein provides for packaging of AAV virus vectors.

Example 8

Propagation of AAV Vector Viruses from a Heterologous Vector Retrovirus Inactivated for ppt Function and Containing Non-Native Vector Components Derived from AAV A retroviral vector DNA construct can be constructed to contain two AAV ITR sequences wherein one is inserted into a site immediately downstream from the primer binding site and the other is inserted into a site from which the ppt sequences were deleted. The AAV rep sequences can be inserted into a site between the ITR sequences (FIG. 9). An Exogenous Nucleic Acid can also be inserted between the AAV ITR sequences.

The sequences for the AAV cap protein and for the retrovirus reverse transcriptase function are inserted into a plasmid such as pBR322. The sequences are expressed under the control of the promoter/enhancer of a constitutive cellular gene such as the elongation factor (EF).

The retroviral vector DNA construct and the plasmid containing the cap and reverse transcriptase sequences are used to cotransfect or sequentially transfect cells. Transcripts of Heterologous Vector RNA are reverse transcribed to yield Heterologous Vector DNA which is single stranded due to the lack of the ppt sequences. In the single stranded DNA product of reverse transcription the AAV ITRs are separated by approximately 4.5 kb and they flank the rep sequence and the Exogenous Nucleic Acid. The rep products can mediate synthesis of single stranded vector DNA wherein the rep sequences and the Exogenous Nucleic Acid are flanked by the AAV ITR sequences. The presence of cap protein provides for packaging of AAV virus vectors.

Example 9

Propagation of AAV Vector Viruses from a Heterologous Vector Retrovirus wherein ppt is Deleted and AAV ITR Sequences Flank the PBS Site A Heterologous Vector (retrovirus vector) DNA construct can be made to contain two AAV ITR sequences that flank the primer binding site (PBS) (FIG. 10). The ppt sequences are removed and the AAV rep sequences are inserted in their place. A Exogenous Nucleic Acid can be inserted between the inserted rep sequence and the downstream ITR sequence.

The sequences for the AAV cap protein and for the retrovirus reverse transcriptase function are inserted into a plasmid such as pBR322. These genes can be expressed under the control of the promoter/enhancer of a constitutive cellular gene such as the elongation factor (EF).

The retroviral vector DNA construct and the plasmid containing the sequences for cap and reverse transcriptase function are used to cotransfect or sequentially transfect cells. Transcripts of Heterologous Vector RNA are reverse transcribed to yield Heterologous Vector DNA which is single stranded due to the lack of the ppt sequences. The rep products can mediate synthesis of single stranded vector DNA wherein the rep sequences and the Exogenous Nucleic Acid are flanked by the AAV ITR sequences wherein the AAV ITR sequences are separated by approximately 4.5 kb. The presence of cap protein provides for packaging of AAV virus vectors.

Example 10

A Heterologous Vector (Retrovirus Vector) that Provides for AAV-Directed Integration of Exogenous Nucleic Acid A Heterologous Vector (retrovirus vector) can be constructed to contain two AAV ITR sequences wherein one is inserted into a site immediately downstream from the primer binding site and the other is inserted into a site just upstream from the retroviral origin for second strand DNA synthesis (ppt) (FIG. 11). The AAV rep sequences are inserted at a site between the two AAV ITR sequences. A Exogenous Nucleic Acid can be inserted between the ITR sequences. Heterologous Vector (retroviruses vector) are produced in retrovirus packaging cells such as the ones described in this patent. The retrovirus vectors are used to transduce target cells wherein the vector RNA undergoes reverse transcription to produce a double stranded DNA. The AAV ITRs and the rep product expressed from the Heterologous Vector can mediate synthesis of single stranded vector DNA wherein the rep sequences and the Exogenous Nucleic Acid are flanked by the AAV ITR sequences. The AAV rep also functions in integration with site specificity for the q13.4-ter region of chromosome 19 of a human target cell.

Example 11

A Heterologous Vector (Retrovirus Vector) with ppt Deleted that Provides for AAV-Directed Integration of Exogenous Nucleic Acid A Heterologous Vector (retrovirus vector) can be constructed to contain two AAV ITR sequences wherein one is inserted into a site immediately downstream from the primer binding site and the other is used to replace the sequences for retroviral origin for second strand DNA synthesis (ppt) (FIG.

12). The AAV rep sequences are inserted at a site between the two AAV ITR sequences. A Exogenous Nucleic Acid can be inserted between the ITR sequences. Such Heterologous Vector (retroviruses vector) are produced in retrovirus packaging cells such as the ones described in this patent. The retrovirus vectors are used to transduce target cells wherein the vector RNA undergoes reverse transcription to produce single stranded Heterologous Vector DNA due to the lack of the ppt sequences. The AAV ITRs and the rep product expressed from the Heterologous Vector can mediate synthesis of single stranded vector DNA wherein the rep sequences and the Exogenous Nucleic Acid are flanked by the AAV ITR sequences. The AAV rep also functions in integration with site specificity for the q13.4-ter region of chromosome 19 of a human target cell.

Example 12

Figure 13:
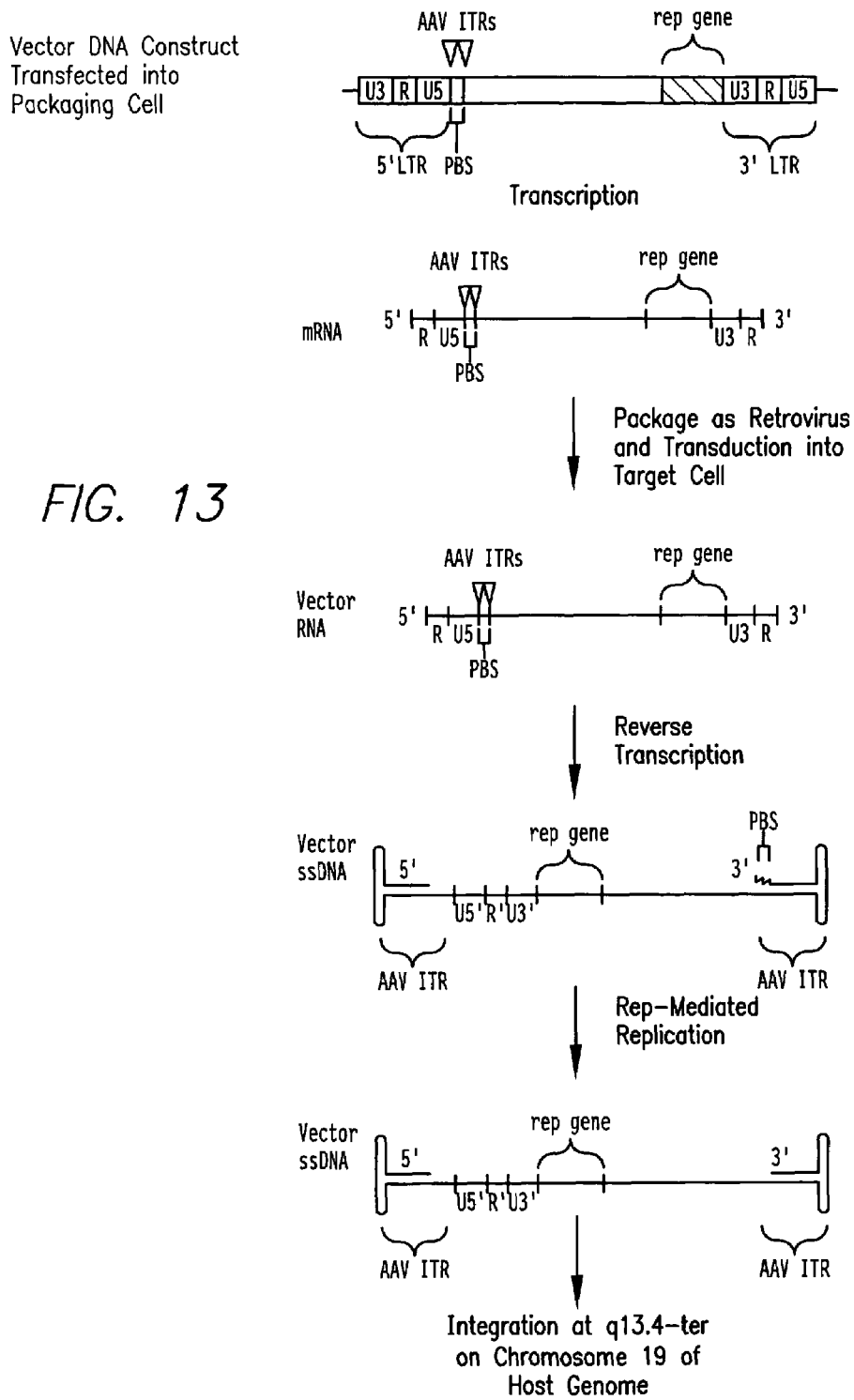
FIG. 13 illustrates the construction of a heterologous vector (retrovirus vector) containing two AAV ITR sequences that flank the primer binding site (PBS). The ppt sequences are removed and the AAV rep sequences are inserted in their place.

A Heterologous Vector (Retrovirus Vector) that Provides for AAV-Directed Integration of Exogenous Nucleic Acid Wherein ppt is Deleted and AAV ITR Sequences Flank the PBS Site A Heterologous Vector (retrovirus vector) can be constructed to contain two AAV ITR sequences which flank the primer binding site (PBS) (FIG. 13). The ppt sequences are removed and the AAV rep sequences are inserted in their place. A Exogenous Nucleic Acid can be inserted between the rep sequence and the downstream ITR sequence. Such Heterologous Vector (retrovirus vectors) are produced in retrovirus packaging cells such as the ones described in this patent. The retrovirus vectors are used to transduce target cells wherein the vector RNA undergoes reverse transcription to produce single stranded Heterologous Vector DNA due to the lack of the ppt sequences. In the single stranded DNA product of reverse transcription the AAV ITRs flank the rep sequence and the Exogenous Nucleic Acid. The AAV ITRs and the rep product expressed from the Heterologous Vector can mediate synthesis of single stranded vector DNA. The AAV rep also functions in integration with site specificity for the q13.4-ter region of chromosome 19 of a human target cell.

Example 13

Use of a Heterologous Vector for the Delivery of Chimeric Antisense RNA Directed Against HIV-1 to CD34 Cells in an Ex Vivo Format A retrovirus vector can be prepared as described in Example 6 which contains a sequence for a chimeric RNA composed of U1 snRNA and an antisense sequence directed against HIV-1. The promoter and enhancer regions of the LTR can be inactivated as described in Example 1. The vector can be constructed to contain no other Heterologous Nucleic Acid and thus cannot produce any protein.

Stromal cultures can be established from bone marrow collection from patients. Cells are plated at a concentration of $3-5\times10^5$ cells/ml in IMDM medium. After generation of the stromal layer, the stromal cells are irradiated and plated at $5\times10^3$ cells per T-25 vent-cap flask in IMDM containing 10% autologous serum on the day before use.

After successful establishment of the stromal culture, leukapheresis of patient blood can begin. Patients undergo leukapheresis following priming with hematapoetic growth factor GCSF by conventional methods. Before leukapheresis, 300 ml of blood is drawn and sterile serum prepared by conventional methods, plasma is collected and white blood cells purified by standard ficoll separation methods. The leukapheresis collections are further purified by Ficoll-Hypaque density gradient centrifugation to separate the PBMC from red cells and neutrophils. The Baxter Isolex procedure can be used to enrich the PBMC fraction for cells expressing CD34+ antigen (stem cells). These cells are eluted from the Baxter column into a tissue culture bag. Cellular phenotype (presence of CD34+ markers) is assessed by flow cytometry prior to expansion.

The cells from the column are expanded in a cell-free, factor-free growth medium supplemented with 10% autologous serum, using the autologous stromal cells as a supporting layer. Stroma is not used until the fourth passage. At this point most hematapoetic cells can be eradicated except for mature macrophages (Nolta, J. A. et al. 1995, incorporated by reference herein). The autologous serum can be filter sterilized and determined to be free of mycoplasma, bacteria and fungi.

The cells are grown in the tissue culture bag for 72 hours. The cells from some patients are grown in the absence of GCSF and the cells from the remaining patients are grown in the presence of GCSF. Before transduction, a sample of CD34+ enriched cells is removed for quantitative measurement of antisense DNA and RNA/cell using PCR and RT/PCR.

The transducing vector can be produced as FDA certified material by appropriate contractors. Vectors consist of high titer (104-106 colony forming units per ml) supernatants of the packaging cell line, PA317. The supernatants are free of pathogens and helper virus.

Cells are resuspended at a concentration of $10^5$ per ml in a transduction medium. The cells are transduced with the MMLV construct (described above) with inactivated 3'-terminal LTR and a sequence for production of a chimeric U1/HIV-1 antisense. After adsorption, fresh medium is added and the cells are grown for one week at 37° C. Aliquots can be stored at all stages.

A sample of CD34+ enriched cells is removed at this time for quantitative measurement of antisense DNA and RNA/cell using PCR and RT/PCR. The transduced cells are grown for 1 week in culture at 37° C. The number of the transduced cells are determined at the end of one week. Samples are prepared for phenotypic analysis. Samples for Gram stain and microbiologic cultures for aerobic and anaerobic bacteria and fungus will be obtained prior to infusion.

The transduced cells are harvested, washed 3 times in normal saline and resuspended in normal saline. The final cell preparation is filtered through a platelet filter and transferred into a transfusion pack for infusion. Intravenous catheterization with standard sterile technique is performed. The infusion can be of not more than $5\times10^8$ cells/kg of body weight. Total volume of infused cells does not exceed 10 ml/kg of body weight. After an initial test infusion of 1-5% of the total volume, cells are infused over the next 60-120 minutes. During infusion, the cell suspension is mixed gently approximately every 5 minutes while the patient is being observed for acute and subacute toxicity.

Patients are monitored for the production of CD4+ cells expressing U1/antisense RNA by RT-PCR as described (Liu, D. et al. 1997 J. Virol. in press, contents incorporated by reference) and for plasma virus concentration and for CD4+ cell count.

Many obvious variations will no doubt be suggested to those of ordinary skill in the art in light of the above detailed description and examples of the present invention. All such variations are fully embraced by the scope and spirit of the invention as more particularly defined by the claims that follow.

What is claimed is:

1. A packaging cell line for propagating a viral vector independent of a helper virus, said viral vector comprising a nucleic acid component and at least two different non-nucleic components, wherein one of said non-nucleic acid components has a tropism for said cell line and the other non-nucleic acid component has a tropism for a target cell which is different from said cell line, said nucleic acid component and said non-nucleic acid components being capable of forming a specific complex or complexes, wherein said sequence or sequences for the viral vector nucleic acid component have been stably integrated in the genome of said cell line, and sequences for the non-nucleic acid components of said viral vector have been stably integrated in the genome of said cell line and code for envelope proteins from two different viruses.

2. The packaging cell line of claim 1, wherein said viral vector comprises a retrovirus or retroviral sequences.

3. The packaging cell line of claim 1, wherein said viral vector nucleic acid component comprises nucleic acid sequences derived from genomic DNA, cDNA, or fragments of either or both of the foregoing.

4. The packaging cell line of claim 1, wherein said packaging cell line and said target cell are from different species.

5. The packaging cell line of claim 1, wherein said target cell comprises T cells, liver cells, bone marrow cells, epithelial cells, or a combination of any of the foregoing.

6. The packaging cell line of claim 1, wherein the viral vector produced from said packaging cell line codes for a protein of interest that is expressed in said target cell.

7. The packaging cell line of claim 1 wherein the viral vector produced from said packaging cell line codes for an antisense RNA that is transcribed in said target cell.

8. The packaging cell line of claim 1, wherein the viral vector produced from said packaging cell line codes for a protein of interest that is expressed in said target cell and for an antisense RNA that is transcribed in said target cell.

9. The packaging cell line of claim 1, wherein said nucleic acid component comprises sequences derived from a virus that has a tropism to said cell line.

10. The packaging cell line of claim 1, wherein said nucleic acid component comprises sequences derived from a virus that has a tropism to said target cell.

11. The packaging cell line of claim 1, wherein said nucleic acid component comprises sequences derived from a virus that has a tropism to said cell line and sequences derived from a different virus that has a tropism to said target cell.

12. The packaging cell line of claim 4, wherein said packaging cell line is a non-human animal species and said target cell is human.

13. The packaging cell line of claim 12, wherein said non-human animal species is murine.

14. The packaging cell line of claim 7, wherein said antisense RNA is complementary to an mRNA coding for a undesirable protein in said target cell.

15. The packaging cell line of claim 7, wherein said antisense RNA is part of a chimeric RNA molecule that comprises sequences from small nuclear RNAs (snRNAs).

16. The packaging cell line of claim 7, wherein said antisense RNA is either (i) complementary to an mRNA coding for a undesirable protein in said target cell or (ii) is part of a chimeric RNA molecule that comprises sequences from small nuclear RNAs (snRNAs).

17. The packaging cell line of claim 8, wherein said antisense RNA is complementary to an mRNA coding for a undesirable protein in said target cell.

18. The packaging cell line of claim 8, wherein said antisense RNA is part of a chimeric RNA molecule that comprises sequences from small nuclear RNAs (snRNAs).

19. The packaging cell line of claim 15, wherein said snRNAs comprises U1, U2, U3, U4, U5, U6, U7, U8, U9, U10 or U11.

20. The packaging cell line of claim 18, wherein said snRNAs comprises U1, U2, U3, U4, U5, U6, U7, U8, U9, U10 or U11.

21. The packaging cell line of claim 16, wherein said snRNAs comprises U1, U2, U3, U4, U5, U6, U7, U8, U9, U10 or U11.

22. A packaging cell line for propagating a viral vector independent of a helper virus, said viral vector comprising a nucleic acid component and at least two different non-nucleic components, wherein one of said non-nucleic acid components has a tropism for said cell line and the other non-nucleic acid component has a tropism for a target cell which is different from said cell line, said nucleic acid component and said non-nucleic acid components being capable of forming a specific complex or complexes, and wherein sequences for the non-nucleic acid components of said viral vector have been stably integrated in the genome of said cell line and code for envelope proteins from two different viruses.

23. The packaging cell line of claim 22, wherein said viral vector comprises a retrovirus or retroviral sequences.

24. The packaging cell line of claim 22, wherein said packaging cell line and said target cell are from different species.

25. The packaging cell line of claim 22, wherein said packaging cell line is a non-human animal species and said target cell is human.

26. The packaging cell line of claim 22, wherein said target cell comprises T cells, liver cells, bone marrow cells, epithelial cells, or a combination of any of the foregoing.

27. The packaging cell line of claim 25, wherein said non-human animal species is murine.

\* \* \* \* \*